United States Patent
Ip et al.

(10) Patent No.: US 10,934,360 B2
(45) Date of Patent: Mar. 2, 2021

(54) HUMAN MONOCLONAL ANTIBODIES AGAINST EPHA4 AND THEIR USE

(71) Applicants: The Hong Kong University of Science and Technology, Hong Kong (CN); THE GOVERNMENT OF THE UNITED STATES OF AMERICA as represented by THE SECRETARY OF THE DEPARTMENT OF HEALTH AND HUMAN SERVICES, Bethesda, MD (US)

(72) Inventors: Nancy Yuk-Yu Ip, Hong Kong (CN); Kit Yu Fu, Hong Kong (CN); Wing Yu Fu, Hong Kong (CN); Dimiter S. Dimitrov, Frederick, MD (US); Tianlei Ying, Frederick, MD (US)

(73) Assignees: The Hong Kong University of Science and Technology, Hong Kong (CN); THE GOVERNMENT OF THE UNITED STATES OF AMERICA as represented by THE SECRETARY OF THE DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 15/329,659

(22) PCT Filed: Jul. 31, 2015

(86) PCT No.: PCT/US2015/043182
§ 371 (c)(1),
(2) Date: Jan. 27, 2017

(87) PCT Pub. No.: WO2016/019280
PCT Pub. Date: Feb. 4, 2016

(65) Prior Publication Data
US 2017/0218075 A1    Aug. 3, 2017

Related U.S. Application Data

(60) Provisional application No. 62/031,793, filed on Jul. 31, 2014.

(51) Int. Cl.
| | | |
|---|---|---|
| C07K 16/28 | (2006.01) | |
| A61K 39/395 | (2006.01) | |
| C07K 14/71 | (2006.01) | |
| A61P 35/00 | (2006.01) | |
| A61P 25/28 | (2006.01) | |
| G01N 33/574 | (2006.01) | |
| G01N 33/68 | (2006.01) | |
| A61K 39/00 | (2006.01) | |

(52) U.S. Cl.
CPC .... *C07K 16/2866* (2013.01); *A61K 39/39558* (2013.01); *A61P 25/28* (2018.01); *A61P 35/00* (2018.01); *C07K 14/71* (2013.01); *G01N 33/57492* (2013.01); *G01N 33/6896* (2013.01); *A61K 2039/505* (2013.01); *C07K 2317/21* (2013.01); *C07K 2317/31* (2013.01); *C07K 2317/55* (2013.01); *C07K 2317/56* (2013.01); *C07K 2317/76* (2013.01); *C07K 2319/30* (2013.01); *G01N 2800/52* (2013.01)

(58) Field of Classification Search
CPC .......... C07K 16/2866; A61K 39/39558; G01N 33/57492
USPC .......................................... 424/133.1, 136.1
See application file for complete search history.

(56) References Cited

U.S. PATENT DOCUMENTS

| | | |
|---|---|---|
| 3,060,165 A | 10/1962 | Craig et al. |
| 4,036,945 A | 7/1977 | Haber |
| 4,235,871 A | 11/1980 | Papahadjopoulos et al. |
| 4,331,647 A | 5/1982 | Goldenberg |
| 4,458,066 A | 7/1984 | Caruthers et al. |
| 4,486,414 A | 12/1984 | Pettit |
| 4,501,728 A | 2/1985 | Geho et al. |
| 4,689,401 A | 8/1987 | Ferris |
| 4,722,848 A | 2/1988 | Paoletti et al. |
| 4,816,444 A | 3/1989 | Pettit et al. |
| 4,837,028 A | 6/1989 | Allen |
| 4,879,278 A | 11/1989 | Pettit et al. |
| 4,892,827 A | 1/1990 | Pastan et al. |
| 4,902,505 A | 2/1990 | Pardridge et al. |
| 4,946,778 A | 8/1990 | Ladner et al. |

(Continued)

FOREIGN PATENT DOCUMENTS

| | | |
|---|---|---|
| CN | 1973040 | 5/2007 |
| CN | 101227921 | 7/2008 |

(Continued)

OTHER PUBLICATIONS

U.S. Appl. No. 97/013,760, filed Apr. 17, 1997, McKeown et al.

(Continued)

*Primary Examiner* — Lynn A Bristol
(74) *Attorney, Agent, or Firm* — Foley & Lardner LLP

(57) ABSTRACT

The present invention provides new, fully human EphA4 monoclonal antibodies with distinct binding characteristics. Also disclosed are antigen binding fragments of these antibodies, bispecific forms of these antibodies, and conjugates of these antibodies. In addition, nucleic acids encoding these antibodies, antigen binding fragments, bispecific antibodies and conjugates are disclosed. These monoclonal antibodies, antigen binding fragments, bispecific antibodies, conjugates, nucleic acids and vectors are of use for identifying and treating a subject with a disease or condition involving abnormal EphA4-mediated signaling.

12 Claims, 13 Drawing Sheets
Specification includes a Sequence Listing.

(56) References Cited

U.S. PATENT DOCUMENTS

| | | |
|---|---|---|
| 4,957,735 A | 9/1990 | Huang |
| 4,978,744 A | 12/1990 | Pettit et al. |
| 4,986,988 A | 1/1991 | Pettit et al. |
| 5,004,697 A | 4/1991 | Pardridge |
| 5,019,369 A | 5/1991 | Presant et al. |
| 5,055,303 A | 10/1991 | Riley, Jr. |
| 5,061,620 A | 10/1991 | Tsukamoto et al. |
| 5,076,973 A | 12/1991 | Pettit et al. |
| 5,079,163 A | 1/1992 | Piatak et al. |
| 5,138,036 A | 8/1992 | Pettit et al. |
| 5,188,837 A | 2/1993 | Domb |
| 5,208,021 A | 5/1993 | Johnson et al. |
| 5,254,342 A | 10/1993 | Shen et al. |
| 5,268,164 A | 12/1993 | Kozarich et al. |
| 5,271,961 A | 12/1993 | Mathiowitz et al. |
| 5,410,024 A | 4/1995 | Pettit et al. |
| 5,413,797 A | 5/1995 | Khan et al. |
| 5,427,930 A | 6/1995 | Birkenmeyer et al. |
| 5,504,191 A | 4/1996 | Pettit et al. |
| 5,506,206 A | 4/1996 | Kozarich et al. |
| 5,512,658 A | 4/1996 | Pastan et al. |
| 5,514,670 A | 5/1996 | Friedman et al. |
| 5,521,284 A | 5/1996 | Pettit et al. |
| 5,530,097 A | 6/1996 | Pettit et al. |
| 5,534,496 A | 7/1996 | Lee et al. |
| 5,554,725 A | 9/1996 | Pettit |
| 5,585,089 A | 12/1996 | Queen et al. |
| 5,587,458 A | 12/1996 | King et al. |
| 5,589,466 A | 12/1996 | Felgner et al. |
| 5,593,972 A | 1/1997 | Weiner et al. |
| 5,599,902 A | 2/1997 | Pettit et al. |
| 5,602,095 A | 2/1997 | Pastan et al. |
| 5,608,039 A | 3/1997 | Pastan et al. |
| 5,635,483 A | 6/1997 | Pettit et al. |
| 5,643,578 A | 7/1997 | Robinson et al. |
| 5,662,907 A | 9/1997 | Kubo et al. |
| 5,663,149 A | 9/1997 | Pettit et al. |
| 5,665,860 A | 9/1997 | Pettit et al. |
| 5,744,311 A | 4/1998 | Fraiser et al. |
| 5,747,498 A | 5/1998 | Schnur et al. |
| 5,780,588 A | 7/1998 | Pettit et al. |
| 5,792,458 A | 8/1998 | Johnson et al. |
| 5,792,783 A | 8/1998 | Tang et al. |
| 5,817,637 A | 10/1998 | Weiner et al. |
| 5,821,238 A | 10/1998 | Pastan et al. |
| 5,834,504 A | 11/1998 | Tang et al. |
| 5,854,044 A | 12/1998 | Pastan et al. |
| 5,861,510 A | 1/1999 | Piscopio et al. |
| 5,863,949 A | 1/1999 | Robinson et al. |
| 5,880,103 A | 3/1999 | Urban et al. |
| 5,883,113 A | 3/1999 | Tang et al. |
| 5,886,020 A | 3/1999 | Tang et al. |
| 6,025,134 A | 2/2000 | Sooknanan |
| 6,033,881 A | 3/2000 | Himmler et al. |
| 6,034,065 A | 3/2000 | Pettit et al. |
| 6,239,104 B1 | 5/2001 | Pettit et al. |
| 6,323,315 B1 | 11/2001 | Pettit et al. |
| 6,884,869 B2 | 4/2005 | Senter et al. |
| 7,498,298 B2 | 3/2009 | Doronina et al. |
| 7,604,799 B2 | 10/2009 | Kinch et al. |
| 8,003,098 B2 | 8/2011 | Nakatsuru et al. |
| 2010/0166657 A1 | 7/2010 | Kinch et al. |
| 2011/0070248 A1 | 3/2011 | Ichikawa et al. |
| 2011/0212088 A1 | 9/2011 | Sabbadini et al. |
| 2013/0288278 A1 | 10/2013 | Inoue |

FOREIGN PATENT DOCUMENTS

| | | |
|---|---|---|
| CN | 101309933 | 11/2008 |
| CN | 101432022 | 5/2009 |
| EP | 0 606 046 A1 | 7/1994 |
| EP | 0 780 386 A1 | 6/1997 |
| EP | 0 931 788 A2 | 7/1999 |
| JP | 2010-285413 A | 12/2010 |
| WO | WO-90/01069 | 2/1990 |
| WO | WO-95/19970 A1 | 7/1995 |
| WO | WO-98/02438 A1 | 1/1998 |
| WO | WO-98/03516 A1 | 1/1998 |
| WO | WO-98/07697 A1 | 2/1998 |
| WO | WO-98/14451 A1 | 4/1998 |
| WO | WO-98/30566 A1 | 7/1998 |
| WO | WO-98/34915 A2 | 7/1998 |
| WO | WO-98/33768 A1 | 8/1998 |
| WO | WO-98/34918 A1 | 8/1998 |
| WO | WO-98/54093 A1 | 12/1998 |
| WO | WO-99/10349 A1 | 3/1999 |
| WO | WO-99/24440 A1 | 5/1999 |
| WO | WO-99/35132 A1 | 7/1999 |
| WO | WO-99/61422 A1 | 12/1999 |
| WO | WO-2005/048917 | 6/2005 |
| WO | WO-2005/048917 A2 | 6/2005 |
| WO | WO-2007/102383 | 9/2007 |
| WO | WO-2007/102383 A1 | 9/2007 |
| WO | WO-2009/032954 A1 | 3/2009 |
| WO | WO-2010/141974 | 12/2010 |
| WO | WO-2010/141974 A1 | 12/2010 |
| WO | WO-2011/032022 A1 | 3/2011 |

OTHER PUBLICATIONS

Altschul et al., "Basic Local Alignment Search Tool," J. Mol. Biol. vol. 215, pp. 403-410, 1990.

Altschul et al., "Gapped BLAST and PSI-BLAST: a new generation of protein database search programs." Nucleic Acids Res., vol. 25, No. 17, pp. 3389-3402 (1997).

Altschul et al., "Issues in searching molecular sequence databases." Nat. Genet., vol. 6, pp. 119-129, Feb. 1994.

Ashida et al., "Molecular Features of the Transition from Prostatic Intraepithelial Neoplasia (PIN) to Prostate Cancer: Genome-wide Gene-expression Profiles of Prostate Cancers and PINs." Cancer Res., vol. 64, No. 17, pp. 5963-5972, Sep. 2004.

Beaucage et al., "Deoxynucleoside phosphoramidites—A new class of key intermediates for deoxypolynucleotide synthesis." Tetra. Lett., vol. 22, No. 20, pp. 1859-1862, 1981.

Buchner et al., "A Method for Increasing the Yield of Properly Folded Recombinant Fusion Proteins: Single-Chain Immunotoxins from Renaturation of Bacterial Inclusion Bodies." Anal. Biochem., vol. 205, pp. 263-270, 1992.

Carmona et al., "Glial ephrin-A3 regulates hippocampal dendritic spine morphology and glutamate transport." Proc. Natl. Acad. Sci., vol. 106, No. 30, pp. 12524-12529, Jul. 2009.

Chen et al., "Eph receptors at synapses: Implications in neurodegenerative diseases." Cellular Signalling, vol. 24, No. 3, pp. 606-611, Mar. 2012.

Corpet, "Multiple sequence alignment with hierarchical clustering," Nucleic Acids Research, vol. 16 No. 22, pp. 10881-10890.

Dalva et al., "EphB Receptors Interact with NMDA Receptors and Regulate Excitatory Synapse Formation." Cell, vol. 103, pp. 945-956, Dec. 2000.

Devereaux et al., "A comprehensive set of sequence analysis programs for the VAX." Nucleic Acids Res., vol. 12, pp. 387-395 (1984).

Easty et al., "Loss of expression o9f receptor tyrosine kinase family genes PTK7 and SEK in metastatic melanoma." Int. J. Cancer vol. 71, pp. 1061-1065, Mar. 1995.

Fu et al., "APCCdh1 mediates EphA4-dependent downregulation of AMPA receptors in homeostatic plasticity." Nat. Neurosci., vol. 14, pp. 181-189, 2011.

Fu et al., "Cdk5 regulates EphA4-mediated dendritic spine retraction through an ephexin1-dependent mechanism." Nat. Neurosci., vol. 10, No. 1, pp. 67-76, 2007.

Funatsu et al., "The Complete Amino Acid Sequence of the A-Chain of Abrin-a, a Toxic Protein from the Seeds of Abrus precatorius." Agric. Biol. Chem., vol. 51, pp. 1095-1097, 1988.

Giaginis et al., "Ephrin (Eph) receptor A1, A4, A5 and A7 expression in human non-small cell lung carcinoma: associations with clinicopathological parameters, tumor proliferative capacity and patients' survival." BMC Clin. Pathol., vol. 14, No. 8, Feb. 2014.

(56) References Cited

OTHER PUBLICATIONS

Gillespie et al., "Phase I open study of the effects of ascending doses of the cytotoxic immunoconjugate CMB-401 (hCTMOI-calicheamicin) in patients with epithelial ovarian cancer." Ann. Oncol., vol. 11, pp. 735-741, 2000.
Goldshmit et al., "EphA4 Blockers Promote Axonal Regeneration and Functional Recovery Following Spinal Cord Injury in Mice." PLoS One, vol. 6:e24636, Sep. 2011.
Goyal & Batra, "Inclusion of a furin-sensitive spacer enhances the cytotoxicity of ribotoxin restrictocin containing recombinant single-chain immunotoxins." Biochem. J., vol. 345, No. 2, pp. 247-254, Jan. 2000.
Hamers-Casterman et al., "Naturally occurring antibodies devoid of light chains." Nature, vol. 363, pp. 446-448, Jun. 1993.
Henikoff et al., "Amino acid substitution matrices from protein blocks," Proc. Natl. Acad. Sci., vol. 89, pp. 10915-10919, Nov. 1992.
Higgins & Sharp, "CLUSTAL: a package for performing multiple sequence alignment on a microcomputer," Gene, vol. 73, 1988, pp. 237-244.
Higgins & Sharp, "Fast and sensitive multiple sequence alignments on a microcomputer," CABIOS Communications, vol. 5, No. 2, pp. 151-153, 1989.
International Search Report issued on PCT/US23015/043182, dated Nov. 13, 2015.
Kondo et al., "Activity of Immunotoxins Constructed with Modified Pseudomonas Exotoxin A Lacking the Cell Recognition Doma." J. Biol. Chem., vol. 263, No. 19, pp. 9470-9475, Jul. 1988.
Laird & Groman, "Prophage Map of Converting Corynebacteriophage Beta." J. Virol., vol. 19, No. 1, pp. 208-219, 1976.
Lee et al., "Calicheamicins, a novel family of antitumor antibiotics. 3. Isolation, purification, and characterization of calicheamicins $\beta 1$ Br, $\gamma 1$ Br, $\alpha 2I$, $\alpha 3I$, $\beta 1I$, $\gamma 1I$ and $\delta 1I$." J. Antibio., vol. 42, pp. 1070-1087, 1989.
Lefranc et al., "IMGT, the international ImMunoGeneTics database." Nucleic Acids Res., vol. 29, No. 1, pp. 207-209, 2001.
Miyazaki et al., "EphA4 is a prognostic factor in gastric cancer." BMC Clin. Pathol., vol. 13, No. 19, 2013.
Needham-Vandevanter et al., "Characterization of an adduct between CC-1065 and a defined oligodeoxynucleotide duplex." Nucleic Acids Res., vol. 12, No. 15, pp. 6159-6168, 1984.
Needleman and Wunsch, J., "A General Method Applicable to the Search for Similarities in the Amino Acid Sequence of Two Proteins," J. Mol. Biol., vol. 48, pp. 443-453, 1970.
Nicolson & Blaustein et al., "The internaction of Ricinus communis agglutinin with normal and tumor cell surfaces." J. Biochim. Biophys. Acta, vol. 266, pp. 543-547, 1972.
Onda et al., "An immunotoxin with greatly reduced immunogenicity by identification and removal of B cell epitopes." Proc. Natl. Acad. Sci., vol. 105, No. 32, pp. 11311-11316, Aug. 2012.
Pack et al., "Improved Bivalent Miniantibodies, with Identical Avidity as Whole Antibodies, Produced by High Cell Density Fermentation of *Escherichia coli*." Nat. Biotechnol., vol. 11, pp. 1271-1277, 1993.
Pai et al., "Anti-tumor activities of immunotoxins made of monoclonal antibody B3 and various forms of Pseudomonas exotoxin." Proc. Natl. Acad. Sci., vol. 88, No. 8, pp. 3358-3362, Apr. 1991.
Pasinelli et al., "Molecular biology of amyotrophic lateral sclerosis: insights from genetics." Nat. Rev. Neurosci., vol. 7, No. 9, pp. 710-723, Sep. 2006.
Pasquale et al., "Eph receptor signalling casts a wide net on cell behavior." Nat. Rev. Mol. Cell Biol., vol. 6, pp. 462-475, Jun. 2005.
Pasquale, "Eph-Ephrin Bidirectional Signaling in Physiology and Disease." Cell, vol. 133, No. 1, Apr. 2008.
Pearson & Lipman, "Improved tools for biological sequence comparison," Proc. Natl. Acad. Sci, vol. 85, pp. 2444-2448, Apr. 1988.
Plückthun, "Antibody Engineering: Advances from the Use of *Escherichia coli* Expression Systems." Biotechnology, vol. 9, pp. 545-551, Jun. 1991.
Porter, "The Hydrolysis of Rabbit $\gamma$-Globulin and Antibodies with Crystalline Papain." Biochem. J., vol. 73, pp. 119-127, 1959.
Prévost et al., "cDNA cloning and tissue distribution of five human EPH-like receptor protein-tyrosine kinases." Proc. Natl. Acad. Sci., vol. 102, pp. 9820-9825, Jul. 2005.
Sheffler-Collins et al., "EphBs: an integral link between synaptic function and synaptopathies." Trends in Neurosci., vol. 35, No. 5, pahes 293-304, May 2012; public access manuscript May 2013.
Siegall et al., "Functional Analysis of Domains II, Ib, and III of Pseudomonas Exotoxin." J. Biol. Chem., vol. 264, Noo. 24, pp. 14256-14261, 1989.
Simón et al., "Early Changes in Hippocampal Eph Receptors Precede the Onset of Memory Decline in Mouse Models of Alzheimer's Disease." J. Alzheimer's Dis., vol. 17, No. 4, pp. 773-786, Jul. 2009.
Smith & Waterman, "Comparison of Biosequences." Adv. Appl. Math. 2, pp. 482-489, 1981.
Weldon et al., "A protease-resistant immunotoxin against CD22 with greatly increased activity against CLL and diminished animal toxicity." Blood, vol. 113, No. 16, pp. 3792-3800, Apr. 2009.
Yamashita et al., "Hypoxia-inducible Transcription Factor-2$\alpha$ in Endothelial Cells Regulates Tumor Neovascularization through Activation of Ephrin A1." J. Biol. Chem., vol. 283, No. 27, pp. 18926-18936, Jul. 2008.
Extended European Search Report issued in European Pat. App. No. 15827008.2 dated Apr. 17, 2018.
Search Report issued on EP Application 15827008.2, dated Jan. 2, 2018.
Office Action dated May 27, 2019 in Japanese Patent Application No. 2017-505223 (6 pages).
Office Action in Japanese Patent Application No. 2017-505223 dated Jan. 14, 2020 (with English translation) (10 pages).
Fu, et al., "Blockade of EphA4 signaling ameliorates hippocampal synaptic dysfunctions in mouse models of Alzheimer's disease," PNAS, Jul. 8, 2014, vol. 111, No. 27, pp. 9959-9964.
Yang Junjie, et al., "Preparation and Analysis of Monocolnal Antibody Against EphA4 Peptide," Journal of Central South University (Medical sciences), vol. 30, No. 5, pp. 529-532.
First Office Action in CN Patent Application No. 201580050476.9 dated May 6, 2020 (with English translation) (12 pages).

SEQUENCE LISTING

```
<160> NUMBER OF SEQ ID NOS: 8

<210> SEQ ID NO 1
<211> LENGTH: 949
<212> TYPE: PRT
<213> ORGANISM: HUMAN

<400> SEQUENCE: 1

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
        115                 120                 125

Ser Asp Asn Asp Lys Glu Arg Phe Ile Arg Glu Asn Gln Phe Val Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
```

```
            195                 200                 205
Arg Asn Leu Ala Gln Phe Pro Asp Thr Ile Thr Gly Ala Asp Thr Ser
210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
        275                 280                 285

Thr Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
            340                 345                 350

Asn Thr Gly Gly Arg Gln Asp Ile Ser Tyr Asn Val Val Cys Lys Lys
        355                 360                 365

Cys Gly Ala Gly Asp Pro Ser Lys Cys Arg Pro Cys Gly Ser Gly Val
    370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
            420                 425                 430

Thr Val Thr Thr Asn Gln Ala Ala Pro Ser Ser Ile Ala Leu Val Gln
        435                 440                 445

Ala Lys Glu Val Thr Arg Tyr Ser Val Ala Leu Ala Trp Leu Glu Pro
    450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510

Val Arg Ala Arg Thr Ala Ala Gly Tyr Gly Asp Phe Ser Glu Pro Leu
        515                 520                 525

Glu Val Thr Thr Asn Thr Val Pro Ser Arg Ile Ile Gly Asp Gly Ala
    530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Arg Ser Lys Tyr
                565                 570                 575

Ser Lys Ala Lys Gln Glu Ala Asp Glu Glu Lys His Leu Asn Gln Gly
            580                 585                 590

Val Arg Thr Tyr Val Asp Pro Phe Thr Tyr Glu Asp Pro Asn Gln Ala
        595                 600                 605

Val Arg Glu Phe Ala Lys Glu Ile Asp Ala Ser Cys Ile Lys Ile Glu
    610                 615                 620
```

```
Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
            660                 665                 670

Ile Met Gly Gln Phe Asp His Pro Asn Ile Ile His Leu Glu Gly Val
        675                 680                 685

Val Thr Lys Cys Lys Pro Val Met Ile Ile Thr Glu Tyr Met Glu Asn
    690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
        755                 760                 765

Arg Val Leu Glu Asp Asp Pro Glu Ala Ala Tyr Thr Thr Arg Gly Gly
    770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
    850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
            900                 905                 910

Val Val Ser Val Gly Asp Trp Leu Gln Val Ile Lys Met Asp Arg Tyr
        915                 920                 925

Lys Asp Asn Phe Thr Ala Ala Gly Tyr Thr Thr Leu Glu Ala Val Val
    930                 935                 940

His Val Asn Gln Glu
945

<210> SEQ ID NO 2
<211> LENGTH: 927
<212> TYPE: PRT
<213> ORGANISM: HUMAN

<400> SEQUENCE: 2

Met Asp Glu Lys Asn Thr Pro Ile Arg Thr Tyr Gln Val Cys Asn Val
1               5                   10                  15

Met Glu Ala Ser Gln Asn Asn Trp Leu Arg Thr Asp Trp Ile Thr Arg
            20                  25                  30

Glu Gly Ala Gln Arg Val Tyr Ile Glu Ile Lys Phe Thr Leu Arg Asp
```

```
                35                  40                  45
Cys Asn Ser Leu Pro Gly Val Met Gly Thr Cys Lys Glu Thr Phe Asn
 50                  55                  60
Leu Tyr Tyr Tyr Glu Ser Asp Asn Asp Lys Glu Arg Phe Ile Arg Glu
 65                  70                  75                  80
Ser Gln Phe Gly Lys Ile Asp Thr Ile Ala Asp Glu Ser Phe Thr
                 85                  90                  95
Gln Val Asp Ile Gly Asp Arg Ile Met Lys Leu Asn Thr Glu Ile Arg
                100                 105                 110
Asp Val Gly Pro Leu Ser Lys Lys Gly Phe Tyr Leu Ala Phe Gln Asp
                115                 120                 125
Val Gly Ala Cys Ile Ala Leu Val Ser Val Arg Val Phe Tyr Lys Lys
                130                 135                 140
Cys Pro Leu Thr Val Arg Asn Leu Ala Gln Phe Pro Asp Thr Ile Thr
145                 150                 155                 160
Gly Ala Asp Thr Ser Ser Leu Val Glu Val Arg Gly Ser Cys Val Asn
                165                 170                 175
Asn Ser Glu Glu Lys Asp Val Pro Lys Met Tyr Cys Gly Ala Asp Gly
                180                 185                 190
Glu Trp Leu Val Pro Ile Gly Asn Cys Leu Cys Asn Ala Gly His Glu
                195                 200                 205
Glu Gln Asn Gly Glu Cys Gln Ala Cys Lys Ile Gly Tyr Tyr Lys Ala
                210                 215                 220
Leu Ser Thr Asp Ala Ser Cys Ala Lys Cys Pro Pro His Ser Tyr Ser
225                 230                 235                 240
Val Trp Glu Gly Ala Thr Ser Cys Thr Cys Asp Arg Gly Phe Phe Arg
                245                 250                 255
Ala Asp Asn Asp Ala Ala Ser Met Pro Cys Thr Arg Pro Pro Ser Ala
                260                 265                 270
Pro Leu Asn Leu Ile Ser Asn Val Asn Glu Thr Ser Val Asn Leu Glu
                275                 280                 285
Trp Ser Ser Pro Gln Asn Thr Gly Gly Arg Gln Asp Ile Ser Tyr Asn
                290                 295                 300
Val Val Cys Lys Lys Cys Gly Ala Gly Asp Pro Ser Lys Cys Arg Pro
305                 310                 315                 320
Cys Gly Ser Gly Val His Tyr Thr Pro Gln Gln Asn Gly Leu Lys Thr
                325                 330                 335
Thr Arg Val Ser Ile Thr Asp Leu Leu Ala His Thr Asn Tyr Thr Phe
                340                 345                 350
Glu Ile Trp Ala Val Asn Glu Val Ser Lys Tyr Asn Pro Ser Pro Asp
                355                 360                 365
Gln Ser Val Ser Val Thr Val Thr Thr Asn Gln Ala Ala Pro Ser Ser
                370                 375                 380
Ile Ala Leu Val Gln Ala Lys Glu Val Thr Arg Tyr Ser Val Ala Leu
385                 390                 395                 400
Ala Trp Leu Glu Pro Asp Arg Pro Asn Gly Val Ile Leu Glu Tyr Glu
                405                 410                 415
Val Lys Tyr Tyr Glu Lys Asp Gln Asn Glu Arg Ser Tyr Arg Ile Val
                420                 425                 430
Arg Thr Ala Ala Arg Asn Thr Asp Ile Lys Gly Leu Asn Pro Leu Thr
                435                 440                 445
Ser Tyr Val Phe His Val Arg Ala Arg Thr Ala Ala Gly Tyr Gly Asp
450                 455                 460
```

```
Phe Ser Glu Pro Leu Glu Val Thr Thr Asn Thr Val Pro Ser Arg Ile
465                 470                 475                 480

Ile Gly Asp Gly Ala Asn Ser Thr Val Leu Val Ser Val Ser Gly
            485                 490                 495

Ser Val Val Leu Val Val Ile Leu Ile Ala Ala Phe Val Ile Ser Arg
            500                 505                 510

Arg Arg Ser Lys Tyr Ser Lys Ala Lys Gln Glu Ala Asp Glu Glu Lys
            515                 520                 525

His Leu Asn Gln Gly Val Arg Thr Tyr Val Asp Pro Phe Thr Tyr Glu
            530                 535                 540

Asp Pro Asn Gln Ala Val Arg Glu Phe Ala Lys Glu Ile Asp Ala Ser
545                 550                 555                 560

Cys Ile Lys Ile Glu Lys Val Ile Gly Val Gly Glu Phe Gly Glu Val
                565                 570                 575

Cys Ser Gly Arg Leu Lys Val Pro Gly Lys Arg Glu Ile Cys Val Ala
            580                 585                 590

Ile Lys Thr Leu Lys Ala Gly Tyr Thr Asp Lys Gln Arg Arg Asp Phe
            595                 600                 605

Leu Ser Glu Ala Ser Ile Met Gly Gln Phe Asp His Pro Asn Ile Ile
610                 615                 620

His Leu Glu Gly Val Val Thr Lys Cys Lys Pro Val Met Ile Ile Thr
625                 630                 635                 640

Glu Tyr Met Glu Asn Gly Ser Leu Asp Ala Phe Leu Arg Lys Asn Asp
                645                 650                 655

Gly Arg Phe Thr Val Ile Gln Leu Val Gly Met Leu Arg Gly Ile Gly
            660                 665                 670

Ser Gly Met Lys Tyr Leu Ser Asp Met Ser Tyr Val His Arg Asp Leu
            675                 680                 685

Ala Ala Arg Asn Ile Leu Val Asn Ser Asn Leu Val Cys Lys Val Ser
            690                 695                 700

Asp Phe Gly Met Ser Arg Val Leu Glu Asp Asp Pro Glu Ala Ala Tyr
705                 710                 715                 720

Thr Thr Arg Gly Gly Lys Ile Pro Ile Arg Trp Thr Ala Pro Glu Ala
            725                 730                 735

Ile Ala Tyr Arg Lys Phe Thr Ser Ala Ser Asp Val Trp Ser Tyr Gly
            740                 745                 750

Ile Val Met Trp Glu Val Met Ser Tyr Gly Glu Arg Pro Tyr Trp Asp
            755                 760                 765

Met Ser Asn Gln Asp Val Ile Lys Ala Ile Glu Glu Gly Tyr Arg Leu
            770                 775                 780

Pro Pro Pro Met Asp Cys Pro Ile Ala Leu His Gln Leu Met Leu Asp
785                 790                 795                 800

Cys Trp Gln Lys Glu Arg Ser Asp Arg Pro Lys Phe Gly Gln Ile Val
            805                 810                 815

Asn Met Leu Asp Lys Leu Ile Arg Asn Pro Asn Ser Leu Lys Arg Thr
            820                 825                 830

Gly Ser Glu Ser Ser Arg Pro Asn Thr Ala Leu Leu Asp Pro Ser Ser
            835                 840                 845

Pro Glu Phe Ser Ala Val Val Ser Val Gly Asp Trp Leu Gln Ala Ile
            850                 855                 860

Lys Met Asp Arg Tyr Lys Asp Asn Phe Thr Ala Ala Gly Tyr Thr Thr
865                 870                 875                 880
```

```
Leu Glu Ala Val Val His Met Ser Gln Asp Asp Leu Ala Arg Ile Gly
            885                 890                 895

Ile Thr Ala Ile Thr His Gln Asn Lys Ile Leu Ser Ser Val Gln Ala
            900                 905                 910

Met Arg Thr Gln Met Gln Gln Met His Gly Arg Met Val Pro Val
        915                 920                 925

<210> SEQ ID NO 3
<211> LENGTH: 126
<212> TYPE: PRT
<213> ORGANISM: HUMAN

<400> SEQUENCE: 3

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Pro Met Val Cys Ser Ser Thr Ser Cys Tyr Leu Arg Gly
            100                 105                 110

Phe Asp Tyr Trp Gly Gln Gly Thr Leu Val Thr Val Ser Ser
        115                 120                 125

<210> SEQ ID NO 4
<211> LENGTH: 126
<212> TYPE: PRT
<213> ORGANISM: HUMAN

<400> SEQUENCE: 4

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Leu Leu Tyr Cys Ser Ser Thr Ser Cys Gly Thr His Gly
            100                 105                 110

Phe Asp Ile Trp Gly Gln Gly Thr Met Val Thr Val Ser Ser
        115                 120                 125

<210> SEQ ID NO 5
<211> LENGTH: 112
<212> TYPE: PRT
<213> ORGANISM: HUMAN
```

-continued

<400> SEQUENCE: 5

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 6
<211> LENGTH: 112
<212> TYPE: PRT
<213> ORGANISM: HUMAN

<400> SEQUENCE: 6

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 7
<211> LENGTH: 112
<212> TYPE: PRT
<213> ORGANISM: HUMAN

<400> SEQUENCE: 7

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ala Phe Gly Gly Gly Thr Lys Val Glu Ile Lys

```
<210> SEQ ID NO 8
<211> LENGTH: 112
<212> TYPE: PRT
<213> ORGANISM: HUMAN

<400> SEQUENCE: 8

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

HUMAN MONOCLONAL ANTIBODIES AGAINST EPHA4 AND THEIR USE

RELATED APPLICATIONS

This application is a 371 U.S. National Stage Application of PCT/US2015/043182, filed Jul. 31, 2015, which claims priority to U.S. Provisional Patent Application No. 62/031,793, filed Jul. 31, 2014, the contents of which are hereby incorporated by reference in their entireties for all purposes.

STATEMENT OF US GOVERNMENT INTERESTS

This invention was made with Government support under project number ZIA BC 010701 by the National Institutes of Health, National Cancer Institute. The U.S. Government has certain rights in the invention.

BACKGROUND OF THE INVENTION

This application relates to monoclonal antibodies (mAbs) and antigen binding fragments or other derivatives thereof that specifically bind EphA4 as well as the use of these antibodies/fragments/derivatives to diagnose and treat diseases and conditions involving deregulated EphA4 signaling, such as tumors, neurodegenerative disorders, and mood disorders.

The erythropoietin-producing hepatocellular (Eph) family of receptors are receptor tyrosine kinases that bind cell membrane anchored ligands and are expressed in at least brain, heart, lung, muscle, kidney, placenta, pancreas (Fox, et al, *Oncogene* (1995) 10:897) and melanocytes (Easty, et al., *Int. J. Cancer* (1997) 71:1061). Eph receptors are divided into two subclasses, EphAs and EphBs (encoded by the genetic loci designated EPHA and EPHB 15 respectively), based on sequence similarity and on their binding affinity for either the glycosylphosphatidylinositol-linked ephrin-A ligands or the transmembrane-bound ephrin-B ligands. There are nine EphAs (EphA1-8 and EphA10) in humans. Binding of ligand to EphA4 results in tyrosine phosphorylation and creates a binding region for proteins with Src Homology 2/3 (SH2/SH3) domains.

EphA4 has been linked to several pathologies and this receptor has been identified as a promising drug target. Modulation of EphA4-ephrin binding has been considered in the treatment of different pathological conditions.

For example EphA4 is expressed on the surface of human platelets, where it promotes thrombus stabilization (Prevost, et al. *Proc Natl Acad Sci USA* (2005) 102: 9820-9825). It is detected in different types of cancer cells (Ashida, et al. *Cancer Res* (2004) 64: 5963-5972) as well as in tumor endothelial cells (Yanmashita, et al. *J. Biol Chem* (2008) 283: 18926-18936). EphA4 has been documented to be up-regulated in breast cancer, esophageal cancer, non-small cell lung carcinoma, gastric cancer and pancreatic cancer (Miyazaki, et al., *BMC Clin Pathol* (2013) 13: 19; Giaginis, et al., *BMC Clin Pathol* (2014)14: 8).

Interfering with the EphA/ephrin-A system to treat diseases of the central nervous system (CNS) has also been investigated. For example, Carmona et al (Carniona, M. A., et al. *Proc Natl Acad Sci US* (2009) 106:12524-9), examines the impact of EphA4 inhibition on glutamate transport. Other studies have identified EphA4 inhibitors as potential therapeutic candidates for the treatment of amyotrophic lateral sclerosis (Van Hoecke, A., et al. *Nat Med* (2012) 18: 1418-1422), and spinal cord injury (Goldshmit, Y., et al. *PLoS One* (2011) 6: e24636). The Eph receptors are also important for the regulation of synapse development and synaptic plasticity (Klein, R. *Nat Neurosci* (2009) 12: 15-20; Pasquale, E. B. *Cell* (2008) 133: 38-52). Whereas EphB enhances synapse development through its interaction with NMDA receptors (Sheffler-Collins, S. I. & Dalva, M. B *Trends in Neurosciences* (2012) 35: 293-304; Dalva, M. B., et al. (2000) *Cell* 103, 945-956), EphA4, which is mainly expressed in the adult hippocampus, acts as a negative regulator of neurotransmission and hippocampal synaptic plasticity (Murai, K. K. & Pasquale, E. B. *Glia* (2011) 59: 1567-1578). Activation of EphA4 by its ligands, ephrins, triggers forward signaling through the induction of receptor clustering and autophosphorylation (Pasquale, E. B. *Nat Rev Mol Cell Biol* (2005) 6: 462-475). This leads to the retraction of dendritic spines through cyclin-dependent kinase 5 (Cdk5)-dependent RhoA activation and reduction of cell adhesion (Fu, W Y., et al. *Nat Neurosci* (2007) 10, 67-76). EphA4 also causes the removal of synaptic and surface AMPA receptors during homeostatic plasticity—a form of plasticity that ensures neuronal output is within the optimal range, thus providing stability for the neuronal network (Chen, Y., Fu, A. K. Y. & Ip, N. Y. *Cellular Signalling* (2012) 24: 606-611; Fu, A. K., et al. *Nat Neurosci* (2011) 14: 181-189). Interestingly, individuals with mild cognitive deficits exhibit deregulated EphB and EphA4 expression (Simon, A. M., et al. *J Alzheimers Dis* (2009) 17: 773-786). More recently, the link between EphA4 signaling and Aβ-induced synaptic failure in Alzheimer's disease (AD) has been investigated. EphA4 mediates hippocampal synaptic dysfunctions in AD and demonstrates that blockade of the ligand-binding domain of EphA4 reverses synaptic impairment in AD mouse models (Fu, A. K., et al. *Proc Natl Acad Sci USA* (2014) 11:9959-9964).

Thus, EphA4 is identified as an important therapeutic target for diseases and disorders of the CNS as well as various cancers of the body. The current invention discloses antibodies that bind human EphA4. These antibodies can be used for the diagnosis and treatment of a subject with a neurodegenerative disease (AD, PD, ALS, MS, etc.), affective disorders such as depression, as well as various forms of cancers, including CNS cancers. Some of these indications are described in greater detail below. These diseases represent an urgent global need as presently there are no effective therapeutic interventions to treat these conditions.

Alzheimer's disease (AD) is marked by gradual but progressive decline in learning and memory, and a leading cause of mortality in the elderly. Currently, an estimated 35 million people worldwide are afflicted with the disease but this figure is expected to rise significantly to 100 million by 2050 due to longer life expectancies. There is no cure and the pathophysiology of the disease is still relatively unknown. There are only four FDA approved drugs available to AD patients, but these only alleviate symptoms rather than alter disease pathology (they cannot reverse the condition or prevent further deterioration) and are ineffective in severe conditions. Thus, early therapeutic intervention is critical in the management of AD. Research has confirmed that AD affects the brain long before actual symptoms of memory loss or cognitive decline actually manifest. However, there are no diagnostic tools for early detection and by the time a patient is diagnosed with AD using current methods, which involves subjective clinical assessment, the pathological symptoms are already at an advanced state.

Parkinson's disease (PD) is the world's second most prevalent neurodegenerative disease after AD. PD is a neurodegenerative disorder that mainly affects the motor system. The motor symptoms of the disease result from the death of dopamine-generating cells in the substantia nigra, a region of the midbrain. The most obvious disease symptoms are movement-related, which include shaking, rigidity, slowness of movement, and difficulty with walking and gait. As the disease progresses, thinking and behavior are affected, with dementia commonly occurring in the advanced stages of the disease. Depression is the most common psychiatric symptom associated with the disease. The major pathological hallmark of the disease is the accumulation of α-synuclein into inclusions called Lewy bodies in neurons, and the death of dopamine-generating cells in the substantia nigra. Currently, PD is diagnosed via clinical symptoms, which include tremors, bradykinesia, rigidity, and postural imbalance, since reliable diagnostic tests or markers for PD are not yet available. Worldwide, it is estimated that ~7 million people have PD. Furthermore, the number of cases is projected to grow significantly due to aging populations. In the US, the number of PD sufferers is predicted to nearly double; but the greatest growth will occur in developing countries in Asia such as China, which is predicted to have an estimated 5 million cases by 2030. However, the actual prevalence of PD is difficult to assess because as the disease is typically not diagnosed until the disease has progressed to an advanced state due to limitations on diagnostic methods.

Amyotrophic lateral sclerosis (ALS), also known as Lou Gehrig's disease, is the most common motor neuron disease with an incidence of 1-2 per 100,000 and a lifetime risk of 1:800. ALS is characterized by a progressive loss of motor neurons from the spinal cord, brainstem, and cerebral cortex, eventually leading to paralysis and death within two to five years of diagnosis. Subjects with ALS have rapidly progressive weakness due to muscle atrophy and muscle spasticity, difficulty in speaking (dysarthria), swallowing (dysphagia), and breathing (dyspnea). Although the order and rate of symptoms varies from person to person, eventually most patients are not able to walk or use their hands and arms, and they lose the ability to speak and swallow their food. Most people with ALS die from respiratory failure, usually within three to five years from the onset of symptoms. The median survival time from onset to death is about three years, and only 4% of patients with this condition survive longer than 10 years. Approximately ten percent of ALS cases are familial forms resulting from highly penetrant monogenic disease-causing mutations. Some specific genes associated with these forms of ALS have been identified, including many known mutations in the superoxide dismutase 1 gene, SOD 1 (Pasinelli and Brown, *Nat Rev Neurosci* (2006) 7:710-23). Loss-of-function mutations in the EPHA4 gene have also been found to be associated with longer survival of patients with amyotrophic lateral sclerosis (ALS) (van Hoecke et al., *Nat Med.* (2012)18(9):1418-22).

Multiple Sclerosis (MS) is an inflammatory degenerative disease where the myelin sheath protecting nerve cells in the brain and spinal cord of the CNS are attacked by the immune system and damaged, thus preventing nerve cell communication within the CNS. The disease is characterized by various symptoms that can include blurry vision, loss of balance, poor coordination, slurred speech, tremors, numbness, extreme fatigue, problems with memory and concentration, paralysis, and blindness. There is no known cure for MS, while clinical interventions aim to improve function after an attack and prevent new attacks. Current drugs however, are moderately effective and have adverse side effects. Worldwide, ~2.3 million people are estimated to be affected by MS. However, MS is typically diagnosed based on signs and symptoms, and even in combination with supporting medical imaging and laboratory testing, diagnosis is difficult. This is especially true in the early stages when symptoms are invisible or similar to other medical conditions.

Clinical depression is a serious, debilitating disorder. According to the World Health Organization, an estimated 350 million people around the world suffer from a severe depressive disorder and it has already become the leading cause of disability worldwide. It is further estimated that clinical depression will affect 17% of the population at least once in their lives. The mean age of onset, from a number of studies, is in the late 20s and about twice as many females as males report clinical depression. Depression is treatable but most people do not receive the care and support they need. Additionally, several FDA-approved drugs are available to ameliorate depressive symptoms. However, patients' responses to the medication vary and there has been a call for more effective treatments.

Given the high prevalence of diseases and conditions involving EphA4 signaling, there exists a distinct need for developing new antibodies that can bind human EphA4 with a high affinity and with desirable effects, e.g., enhancing or suppressing EphA4-mediated signaling by virtue of their binding to EphA4. These antibodies are valuable tools for the diagnosis and/or treatment of various diseases and conditions involving deregulated EphA4 signaling. Such diseases and disorders include various types of cancers, neurodegenerative diseases (such as Alzheimer's disease (AD), Parkinson's disease (PD), multiple sclerosis (MS), amyotrophic lateral sclerosis (ALS), and affective disorder such as depression. The present invention addresses these and other related needs.

BRIEF SUMMARY OF THE INVENTION

The invention provides new monoclonal antibodies that specifically bind EphA4 with a high affinity and distinct effects. Also disclosed are antigen binding fragments of these antibodies, bispecific forms of these antibodies, and derivatives of the antibodies or their fragments such as conjugates of these antibodies with an effector molecule, including various fusion proteins comprising one of the antibodies or fragments. In addition, disclosed are nucleic acids encoding these antibodies, antigen binding fragments, bispecific antibodies and conjugates in the form of fusion proteins. In some embodiments, expression cassettes and vectors are disclosed including these nucleic acids, and host cells including these vectors or cassettes. In further embodiments, pharmaceutical compositions include these monoclonal antibodies, antigen binding fragments, bispecific antibodies, conjugates, nucleic acids and vectors. In yet other embodiments, these monoclonal antibodies, antigen binding fragments, bispecific antibodies, conjugates, nucleic acids and vectors are of use for identifying and treating a subject with a tumor. In additional embodiments, these monoclonal antibodies, antigen binding fragments, bispecific antibodies, conjugates, nucleic acids and vectors are of use for identifying and treating a subject with a neurodegenerative disorder such as AD, PD, MS, or ALS.

In some embodiments, an isolated monoclonal antibody or an antigen binding fragment thereof includes: a) a heavy chain variable domain including amino acids 26-33 of the amino acid sequence set forth as SEQ ID NO:3, amino acids 51-58 of the amino acid sequence set forth as SEQ ID NO:3, and/or amino acids 97-115 of the amino acid sequence set forth as SEQ ID NO:3 and a light chain variable domain including amino acids 27-37 of the amino acid sequence set forth as SEQ ID NO:6, amino acids 55-57 of the amino acid sequence set forth as SEQ ID NO:6, and/or amino acids 94-100 of the amino acid sequence set forth as SEQ ID NO:6; b) a heavy chain variable domain including amino acids 26-33 of the amino acid sequence set forth as SEQ ID NO:4, amino acids 51-58 of the amino acid sequence set forth as SEQ ID NO:4, and/or amino acids 97-115 of the amino acid sequence set forth as SEQ ID NO:4 and a light chain variable domain including amino acids 27-37 of SEQ ID NO:7, amino acids 55-57 of the amino acid sequence set forth as SEQ ID NO:7, and/or amino acids 94-100 of the amino acid sequence set forth as SEQ ID NO:7; or c) a heavy chain variable domain including amino acids 27-37 of the amino acid sequence set forth as SEQ ID NO:5, amino acids 55-57 of the amino acid sequence set forth as SEQ ID NO:5, and/or amino acids 94-100 of the amino acid sequence set forth as SEQ ID NO:5 and a light chain variable domain including amino acids 27-37 of the amino acid sequence set forth as SEQ ID NO:8, amino acids 55-57 of the amino acid sequence set forth as SEQ ID NO:8, and/or amino acids 94-100 of the amino acid sequence set forth as SEQ ID NO:8, wherein the monoclonal antibody or antigen binding fragment specifically binds EphA4.

In other embodiments, disclosed are an isolated monoclonal antibody or antigen binding fragment that includes: a) a heavy chain variable domain including amino acids 26-33 of the amino acid sequence set forth as SEQ ID NO:3, amino acids 51-58 of the amino acid sequence set forth as SEQ ID NO:3, and amino acids 97-115 of the amino acid sequence set forth as SEQ ID NO:3 and a light chain variable domain including amino acids 27-37 of the amino acid sequence set forth as SEQ ID NO:6, amino acids 55-57 of the amino acid sequence set forth as SEQ ID NO:6, and amino acids 94-100 of the amino acid sequence set forth as SEQ ID NO:6; b) a heavy chain variable domain including amino acids 26-33 of the amino acid sequence set forth as SEQ ID NO:4, amino acids 51-58 of the amino acid sequence set forth as SEQ ID NO:4, and amino acids 97-115 of the amino acid sequence set forth as SEQ ID NO:4 and a light chain variable domain including amino acids 27-37 of SEQ ID NO:7, amino acids 55-57 of the amino acid sequence set forth as SEQ ID NO:7, and amino acids 94-100 of the amino acid sequence set forth as SEQ ID NO:7; or c) a heavy chain variable domain including amino acids 27-37 of the amino acid sequence set forth as SEQ ID NO:5, amino acids 55-57 of the amino acid sequence set forth as SEQ ID NO:5, and amino acids 94-100 of the amino acid sequence set forth as SEQ ID NO:5 and a light chain variable domain including amino acids 27-37 of the amino acid sequence set forth as SEQ ID NO:8, amino acids 55-57 of the amino acid sequence set forth as SEQ ID NO:8, and amino acids 94-100 of the amino acid sequence set forth as SEQ ID NO:8.

Thus, in the first aspect, the present invention provides an anti-EphA4 antibody, especially a monoclonal antibody, having the heavy chain ($V_H$) and light chain ($V_L$) variable domains as described above (e.g., SEQ ID NO:3 and SEQ ID NO:6; SEQ ID NO:4 and SEQ ID NO:7; or SEQ ID NO:5 and SEQ ID NO:8), especially with the $V_H$ and $V_L$ CDRs as specified above, or a heavy chain or a light chain of the antibody, a binding fragment of the antibody, a bispecific antibody comprising such a binding fragment, or a derivative therefore such as a fusion protein or conjugate with another functional moiety, e.g., to facilitate detection or to provide a specific biological activity.

In some embodiments, the antibody or antigen binding fragment is fully human. In some embodiments, the antibody is an IgG. In some embodiments, the antigen binding fragment is an scFv, Fv, Fab, or F(ab)2 antigen binding fragment. In some embodiments, the antibody of this invention is a bispecific antibody comprising the antibody or antigen biding fragment described herein. In some embodiments, the antibody or antigen binding fragment or the bispecific antibody thereof is conjugated to an effector molecule, which may be a detectable label, such as a fluorescent marker, radiolabel, avidin, biotin, or an enzyme, or which may be a toxin or a chemotherapeutic agent, such as a *Pseudomonas* exotoxin.

In a second aspect, the present invention provides a polynucleotide sequence encoding the antibody or antigen binding fragment or the bispecific antibody or the fusion polypeptide conjugate thereof. Optionally, the polynucleotide coding sequence is operably linked to a promoter, especially a heterologous promoter. In some embodiments, an expression cassette is provided that comprises the polynucleotide sequence described above. In some embodiments, the polynucleotide coding sequence or the expression cassette is present as a part of a vector, such as a viral vector. In some embodiments, the vector or expression cassette is present in a host cell in a transient or permanent manner.

In a third aspect, the present invention provides a method of detecting ephrin EphA4 in a biological sample. The method comprises these steps: contacting the sample with the antibody or antigen binding fragment or the bispecific antibody or the conjugate described herein under conditions sufficient to form an immune complex; and detecting the presence or absence of the immune complex, wherein the presence of the immune complex indicates that EphA4 is present in the biological sample. In some embodiments, the sample is from a human subject or from a murine subject. In some embodiments, the sample is contacted with a conjugate described herein.

In a fourth aspect, the present invention provides a method of detecting the presence of a tumor in a subject. The method comprises these steps: contacting a biological sample from the subject suspected of having the tumor with an effective amount of the monoclonal antibody or antigen binding fragment or bispecific antibody or the conjugate described herein; and detecting binding of the monoclonal antibody, antigen binding fragment, or the bispecific antibody, wherein an increase in binding of the monoclonal antibody, antigen binding fragment, bispecific antibody or conjugate as compared to a control indicates that the subject has the tumor. In some embodiments, the control is a reference standard or the binding of the monoclonal antibody, antigen binding fragment, bispecific antibody to a sample from a healthy subject not suffering from a tumor. In some embodiments, the tumor is a breast carcinoma, esophageal cancer, non-small cell lung cancer, gastric cancer and pancreatic cancer. In some embodiments, the sample is a blood, serum, plasma, sputum, or a biopsy sample.

In a fifth aspect, the present invention provides a method of determining the prognosis of a subject with a tumor. The method comprises these steps: contacting a biological sample from the subject suspected of having the tumor with an effective amount of the antibody or antigen binding fragment or bispecific antibody or the conjugate described herein; and detecting binding of the monoclonal antibody, antigen binding fragment, bispecific antibody, or conjugate to the sample, wherein an increase in binding of the monoclonal antibody, antigen binding fragment, bispecific antibody or conjugate as compared to a control indicates a poor prognosis for the subject with the tumor. In some embodiments, the control is a reference standard or the binding of the monoclonal antibody, antigen binding fragment or bispecific antibody to a sample from a healthy subject who does not have any tumor. In some embodiments, the tumor is a breast carcinoma, esophageal cancer, non-small cell lung cancer, gastric cancer and pancreatic cancer. In some embodiments, the sample is a blood, serum, plasma, sputum, or a biopsy sample.

In a sixth aspect, the present invention provides a method for treating a subject with a tumor, comprising administering to the subject a therapeutically effective amount of the antibody or antigen binding fragment or bispecific antibody or the conjugate described herein, thereby treating the tumor. In some embodiments, the tumor is a breast carcinoma, esophageal cancer, non-small cell lung cancer, gastric cancer and pancreatic cancer. In some embodiments, the treating comprises reducing tumor volume or decreasing metastasis.

In a seventh aspect, the present invention provides a method of detecting the presence or assessing the risk of developing neurodegeneration or an affective disorder in a subject. The method comprises these steps: contacting a biological sample from a subject with an effective amount of the antibody or antigen binding fragment or bispecific antibody or the conjugate described herein; and detecting binding of the monoclonal antibody, antigen binding fragment, or the bispecific antibody or the conjugate to EphA4, wherein an increase in binding of the monoclonal antibody, antigen binding fragment, bispecific antibody or conjugate to EphA4 in the biological sample as compared to a control indicates that the subject has or is at an elevated risk of developing the neurodegeneration or the affective disorder. In some embodiments, the control is a reference standard or the binding of the monoclonal antibody, antigen binding fragment, bispecific antibody or conjugate to EphA4 in a sample from a healthy subject not suffering from or at risk of developing neurodegeneration or an affective disorder. In some embodiments, the neurodegeneration is AD, PD, MS, or ALS, which may be familial or sporadic. In some embodiments, the affective disorder is depression.

In an eighth aspect, the present invention provides a method of determining the prognosis of neurodegeneration or an affective disorder in a subject. The method comprises these steps: contacting a biological sample from the subject with the neurodegeneration or effective disorder with an effective amount of the antibody or antigen binding fragment or bispecific antibody or the conjugate described herein; and detecting binding of the antibody, antigen binding fragment, bispecific antibody, or conjugate to EphA4 in the biological sample, wherein an increase in binding of the antibody, antigen binding fragment, bispecific antibody or conjugate to EphA4 as compared to a control indicates a poor prognosis for the subject. In some embodiments, the control is a reference standard or the binding of the monoclonal antibody, antigen binding fragment bispecific antibody or conjugate to EphA4 a sample from a healthy subject not suffering from neurodegeneration or an affective disorder. In some embodiments, the neurodegeneration is AD, PD, MS, or ALS. The ALS may be familiar or sporadic. In some embodiments, the sample is a blood, serum, plasma, sputum, or a biopsy sample. In some embodiments, the affective disorder is depression.

In a ninth aspect, the present invention provides a method for treating a subject with neurodegeneration or an affective disorder. The method includes the step of administering to the subject a therapeutically effective amount of the antibody or antigen binding fragment or bispecific antibody or the conjugate described herein, thereby treating the neurodegeneration or effective disorder. In some embodiments, the neurodegeneration is AD, PD, MS, or ALS (including familial or sporadic ALS). In some embodiments, the affective disorder is depression. In some embodiments, the monoclonal antibody is IgG1 m105.

In a tenth aspect, the present invention provides a pharmaceutical composition comprising a therapeutically effective amount of the antibody or antigen binding fragment or or the conjugate described herein, a nucleic acid encoding the antibody, antigen binding fragment, bispecific antibody or conjugate, and a pharmaceutically acceptable carrier. In some embodiments, the pharmaceutical composition is formulated for sustained release. In some embodiments, the pharmaceutical composition comprises the monoclonal antibody IgG1 m101, IgG1 m105, or IgG1 m119.

DEFINITIONS

Figure 1:
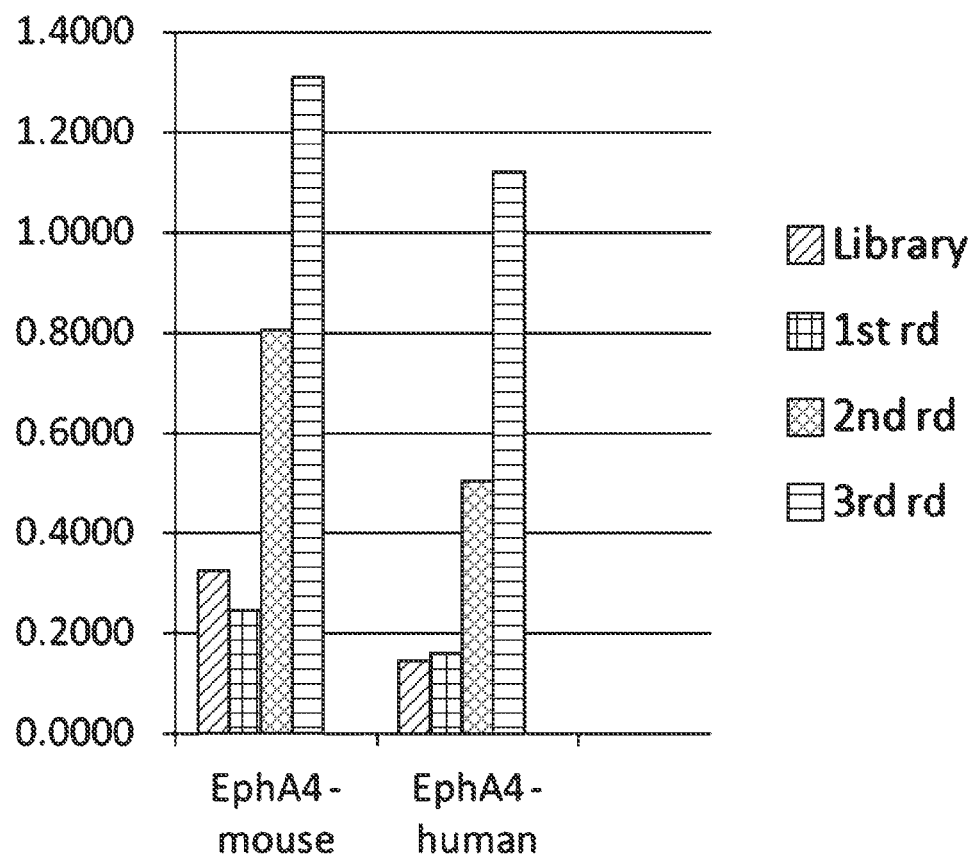
FIG. 1. Polyclonal phage ELISA of phages from library, $1^{st}$ round, $2^{nd}$ round, and $3^{rd}$ round of panning. Phages were added to mouse EphA4 or human EphA4 coated wells. HRP-conjugated anti-M13-phage Ab was used for detection.

Administration: The introduction of a composition into a subject by a chosen route. For example, if the chosen route is intravenous, the composition is administered by introducing the composition into a vein of the subject.

Amyotrophic Lateral Sclerosis (ALS): A disease also called Lou Gehrig's Disease, Maladie de Charcot or motor neuron disease that is a progressive, fatal, neurodegenerative disease caused by the degeneration of motor neurons. The disorder causes muscle weakness and atrophy throughout the body as both the upper and lower motor neurons degenerate and die so that they no longer innervate the muscles. The muscles gradually weaken, atrophy and develop fasciculations (twitches) because of denervation. Eventually, the brain completely loses its ability to initiate and control voluntary movement. The disease does not necessarily debilitate the patient's mental functioning. Generally, subjects in the advanced stages of the disease retain the same memories, personality, and intelligence they had before its onset. ALS is classified into two groups, familial ALS and sporadic ALS. "Late-onset" ALS develops in individuals over the age of 60. "Early onset" ALS develops in subjects younger than 60 years of age.

The earliest symptoms of ALS may include twitching, cramping, or stiffness of muscles; muscle weakness affecting an arm or a leg; and/or slurred and nasal speech. These general complaints then develop into more obvious weakness or atrophy. The parts of the body affected by early symptoms of ALS depend on which muscles in the body are damaged first. About 75% of people experience "limb onset" ALS. Generally, in "limb-onset" ALS the symptoms first appear in a limb. In some subjects, symptoms initially affect one of the legs, and patients experience awkwardness when walking or running or they notice that they are tripping or stumbling more often. Other limb onset patients first see the effects of the disease on a hand or arm as they experience difficulty with simple tasks requiring manual dexterity such as buttoning a shirt or writing. About 25% of ALS cases are "bulbar onset" ALS. These patients first notice difficulty speaking clearly; their speech becomes garbled and slurred. Nasality and loss of volume are frequently the first symptoms; difficulty swallowing, and loss of tongue mobility follow. Eventually total loss of speech and the inability to protect the airway when swallowing are experienced.

Regardless of the part of the body first affected by the disease, muscle weakness and atrophy spreads to other parts of the body as the disease progresses. Patients experience increasing difficulty moving, swallowing (dysphagia), and speaking or forming words (dysarthria). Symptoms of upper motor neuron involvement include tight and stiff muscles (spasticity) and exaggerated reflexes (hyperreflexia) including an overactive gag reflex. An abnormal reflex commonly called Babinski's sign (the large toe extends upward as the sole of the foot is stimulated) also indicates upper motor neuron damage. Symptoms of lower motor neuron degeneration include muscle weakness and atrophy, muscle cramps, and fleeting twitches of muscles that can be seen under the skin (fasciculations). Around 15-45% of patients experience pseudobulbar affect, also known as "emotional liability," which consists of uncontrollable laughter, crying or smiling.

RILUZOLE™ (Rilutek) is used to treat ALS. This drug is believed to reduce damage to motor neurons by decreasing the release of glutamate. Clinical trials with ALS patients showed that riluzole prolongs survival by several months, and may have a greater survival benefit for those with a bulbar onset. The drug also extends the time before a patient needs ventilation support.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and specifically binds an epitope of an antigen, such as human EphA4 and/or mouse EphA4, or a fragment thereof. Immunoglobulin molecules are composed of a heavy and a light chain, each of which has a variable region, termed the variable heavy ($V_H$) region and the variable light ($V_L$) region. Together, in a native antibody, the $V_H$ region and the $V_L$ region bind the antigen recognized by the antibody. In some embodiments, only the heavy chain variable domain is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996).

Antibodies include intact immunoglobulins. Antigen binding fragments are well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined. See, for example, Kabat et al. (see, Kabat et al., *Sequences of Proteins of Immunological Interest*, U.S. Department of Health and Human Services, 1991) and ImMunoGeneTies database (IMGT) (see, Lefranc, *Nucleic Acids Res* 29:207-9, 2001; and //imgt.cines.fr/IMGT_vquest/vquest?livret=0&Option=humanIg;). The Kabat database is now maintained online (ncbi.nlm.nih.gov/igblast/). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 (or H-CDR3) is located in the variable domain of the heavy chain of the antibody in which it is found, whereas a $V_L$ CDR1 (Or L-CDR1) is the CDR1 from the variable domain of the light chain of the antibody in which it is found. An antibody that binds EphA4, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" or a "mAb" is an antibody produced by a single clone of B-lymphocytes or by a cell into which the light and heavy chain genes of a single antibody have been transfected. MAbs are produced by methods known to those of skill in the art, for instance by making hybrid antibody-forming cells from a fusion of myeloma cells with immune spleen cells. MAbs include humanized mAbs.

A "chimeric antibody" has framework residues from one species, such as human, and CDRs (which generally confer antigen binding) from another species, such as a murine antibody that specifically binds EphA4.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other mAbs can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigenic epitope, such as and epitope of human EphA4 and/or mouse EphA4 with a high affinity, and does not significantly bind other unrelated epitopes.

Bi-specific antibody: A recombinant molecule composed of two different antigen binding moieties and consequently binds to two different antigenic epitopes. Bi-specific antibodies include chemically or genetically linked molecules of two antigen-binding moieties. The antigen binding moieties can be linked using a linker. The antigen binding moieties can be monoclonal antibodies, antigen-binding fragments (e.g., Fab, scFv), eAds, or combinations thereof. A bispecific antibody can include one or more constant domains, but does not necessarily include a constant domain.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a lymphoma, leukemia, or another tumor. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, *Clinical Oncology* $2^{nd}$ ed., ©2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds EphA4 or a fragment thereof used in combination with a radioactive or chemical compound.

Conservative variants: "Conservative" amino acid substitutions are those substitutions that do not substantially affect or decrease the affinity of a protein, such as an antibody that specifically binds EphA4. For example, a human antibody that specifically binds EphA4 can include at most about 1, at most about 2, at most about 5, and most about 10, or at most about 15 conservative substitutions and specifically bind the EphA4 polypeptide. The term conservative variation also includes the use of a substituted amino acid in place of an unsubstituted parent amino acid, provided that antibody specifically binds EphA4. Non-conservative substitutions are those that reduce an activity or binding to EphA4.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a polypeptide, such as n EphA4 polypeptide or an antibody that binds EphA4, that includes a sequence that is degenerate as a result of the genetic code. There are 20 natural amino acids, most of which are specified by more than one codon. Therefore, all degenerate nucleotide sequences are included as long as the amino acid sequence of polypeptide, such as the EphA4 polypeptide or antibody that binds EphA4, that is encoded by the nucleotide sequence is unchanged.

Diagnostic: Identifying the presence or nature of a pathologic condition, such as, but not limited to, cancer or ALS. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or ALS.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-EphA4 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Erythropoietin-producing hepatocellular (Eph)A4: A receptor tyrosine kinase that is expressed in brain, heart, lung, muscle, kidney, placenta, pancreas (Fox, et al, Oncogene 10:897, 1995) and melanocytes (Easty, et al., Int. J. Cancer 71:1061, 1997). EphA4 binds cell membrane-anchored ligands (Ephrins A1, A2, A3, A4, A5, B2, and B3; Pasquale, Curr. Opin. in Cell Biology, 1997, 9:608; also ligands B61, AL1/RAGS, LERK4, Htk-L, and Elk-L3; Martone, et al., Brain Research 771:238, 1997), and ligand binding leads to EphA4 autophosphorylation on tyrosine residues (Ellis, et al., Oncogene 12:1727, 1996). EphA4 tyrosine phosphorylation creates a binding region for proteins with Src Homology 2/3 (SH2/SH3) domains, such as the cytoplasmic tyrosine kinase p59fyn (Ellis, et al., supra; Cheng, et al., Cytokine and Growth Factor Reviews 13:75, 2002). Exemplary amino acid sequences of human and mouse EpHA4 are provided below.

Engineered antibody domain (eAd): Also known as a "single domain antibody," this molecule is a single monomeric variable antibody domain. The variable region includes complementarity determining regions (CDRs) that confer binding specificity, and framework regions, which are those parts of the variable domain other than the CDRs. Generally, an eAd has a molecular weight of only 12-15 kDa, and thus is smaller than a mAb with two heavy chains and two light chains (approximately 150-160 kDa) and Fab fragments (approximately 50 kDa). In one embodiment, an eAd includes a variable heavy chain domain with H-CDR1, H-CDR2 and H-CDR3, and specifically binds a target antigen, but does not include light chain CDRs or a light chain variable domain. eAds are highly expressed in microbial cell culture, show favorable biophysical properties including solubility and temperature stability, and are well suited to selection and affinity maturation by in vitro selection systems such as phage display. eAds also are bioactive as monomers and, due to their small size and inherent stability, can be formatted into larger molecules to create drugs with prolonged serum half-lives or other pharmacological activities. An eAd can include any suitable framework region and can be human or humanized.

Epitope: An antigenic determinant. These are particular chemical groups or peptide sequences on a molecule that are antigenic, i.e. that elicit a specific immune response. An antibody specifically binds a particular antigenic epitope on a polypeptide, such as human EphA4 and/or mouse EphA4.

Expressed: Translation of a nucleic acid into a protein. Proteins may be expressed and remain intracellular, become a component of the cell surface membrane, or be secreted into the extracellular matrix or medium.

Expression cassette: A nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed (e.g., one encoding an anti-EphA4 antibody or a binding fragment thereof), operably linked to a promoter.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework region: Amino acid sequences interposed between CDRs. Framework regions include variable light and variable heavy framework regions. The framework regions serve to hold the CDRs in an appropriate orientation for antigen binding.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody, antigen binding fragment thereof or bispecific antibody. The effector molecule can be a detectable label or an immunotoxin. Specific, non-limiting examples of toxins include, but are not limited to, abrin, ricin, *Pseudonmonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule. Immunoconjugates are non-naturally occurring molecules.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of human EphA4, or a fragment thereof, wherein the polypeptide that is expressed on the cell surface of a host cell that expresses the full-length human EphA4 polypeptide.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for a disease such as a tumor (for example, a cancer such as breast cancer) or a motor neuron disease such as ALS. "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. In some embodiments, the biological component is at least 95%, 96%, 97%, 98% or 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide, such as within an antibody binding fragment (such as an Fv fragment), which serves to indirectly bond the variable heavy chain to the variable light chain. "Linker" can also refer to a peptide serving to link a targeting moiety, such as an antibody, to an effector molecule, such as a cytotoxin or a detectable label. The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). In several examples, a tumor is breast carcinoma, esophageal cancer, non-small cell lung cancer, gastric cancer and pancreatic cancer.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov/). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 9 to 12 amino acids in length.

A "human EphA4 peptide" is a series of contiguous amino acid residues from a human EphA4 protein. A "mouse EphA4 peptide" is a series of contiguous amino acid residues from an mouse EphA4 protein.

In one example, with respect to immunogenic compositions comprising an human EphA4 peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a Major Histocompatibility Complex Class I molecule, to activate cytotoxic T lymphocytes against cells expressing wild-type human EphA4 protein. Induction of CTLs using synthetic peptides and CTL cytotoxicity assays are taught in, for example, U.S. Pat. No. 5,662,907.

Peptide modifications: Polypeptides, such as EphA4 polypeptides, include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_6$ alkyl, or combined to form a heterocyclic ring, such as a 5- or 6-membered ring. Amino groups of the peptide, whether amino-terminal or side chain, may be in the form of a pharmaceutically-acceptable acid addition salt, such as HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_6$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the EphA4 peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a EPHA4 polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden, a decrease in the number of size of metastases, or an increase in motor skills. "Ameliorating" refers to the reduction in the number or severity of signs or symptoms of a disease, such as a tumor or ALS.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

The EphA4 polypeptides disclosed herein, antibodies that specifically bind EphA4, antigen binding fragments and bispecific antibodies can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Recombinant toxins: Chimeric proteins in which a cell targeting moiety, such as an antibody, antigen binding fragment, or bispecific antibody is fused to a toxin (Pastan et al., *Science*, 254:1173-1177, 1991). If the cell targeting moiety is the Fv portion of an antibody, the molecule is termed a recombinant immunotoxin (Chaudhary et al., *Nature,* 339: 394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used, for example, to treat a tumor, for example, a tumor in which human EphA4 is expressed. The recombinant toxins are non-naturally occurring.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a HCC tissue biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds an EphA4 polypeptide are typically characterized by possession of at least about 75%, for example at least about 80%, 90%, 95%, 96%, 97%. 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an EphA4 specific binding agent is an agent that binds substantially to an EphA4 polypeptide, such as human and/or mouse EphA4. In one embodiment, the specific binding agent is a human monoclonal antibody, antigen binding fragment thereof, or bispecific antibody that specifically binds the EphA4 polypeptide.

The term "specifically binds" refers, with respect to an antigen such as EphA4, to the preferential association of an antibody or other ligand, in whole or part, with a cell or tissue bearing that antigen and not to cells or tissues lacking that antigen, such as a cell that expresses a different EphA. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the EphA4 polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select mAbs specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain 1a of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The phrase "A or B" is intended to include A, B and both A and B, unless the context clearly indicates otherwise. Hence "comprising A or B" means including A, B, or "A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GENBANK® Accession numbers are herein incorporated by reference as they appear in the database on Sep. 5, 2011. In case of conflict, the present specification, including explanations of terms, will control. In addition, the materials, methods, and examples are illustrative only and not intended to be limiting.

DETAILED DESCRIPTION OF THE INVENTION

I. Introduction

The present invention provides monoclonal antibodies that specifically bind EphA4, as well as antigen binding fragments of these antibodies (such as single chain antibodies, Fab or F(ab')$_2$, variable regions of the heavy or light chain, i.e., $V_H$ or $V_L$), bispecific forms of these antibodies, and conjugates (including those in the form of fusion proteins) of these antibodies/fragments with one or more effector molecules. In addition, disclosed are nucleic acids encoding these antibodies, antigen binding fragments, bispecific antibodies, and conjugates in the form of fusion proteins. In some embodiments, vectors are disclosed including these nucleic acids, and host cells including these vectors. In further embodiments, pharmaceutical compositions include these monoclonal antibodies, antigen binding fragments, bispecific antibodies, conjugates, nucleic acids and vectors. These monoclonal antibodies, antigen binding fragments, bispecific antibodies, conjugates, nucleic acids and vectors are of use for identifying and treating a subject with a tumor, and are also of use for identifying and treating a subject with a neurodegenerative disease (e.g., AD, PD, ALS, MS, etc) or an affective disorder such as depression.

More specifically, this invention encompasses several fully human monoclonal EphA4 antibodies with distinct activities. IgG1s m101, m105, and m119 specifically recognize the ligand binding domain of EphA4. For example, IgG1 m105 specifically inhibits interaction of EphA4 with ephrin-A/B but does not interfere with the interaction between ephrin-B and EphB2 receptor. The antibodies also exhibit a strong binding affinity to the EphA4 ligand binding domain. The m101 and m119 IgG1s bind to human and mouse EphA4 with an EC50 of 1 nmoL/L, while the m105 IgG1 binds to human and mouse EphA4 with subnanomolar EC50. Furthermore, IgG1 m119 acts as an agonistic antibody by stimulating EphA4 activation, while IgG1 m105 acts as an EphA4 antagonist that attenuates ephrin-A1-induced EphA4 activation. The antagonistic activity of IgG1 m105 makes this antibody a potentially highly effective therapeutic tool for treating neurodegenerative diseases such as AD, PD, MS, or ALS. IgG1 m105 does not affect the binding of EphB and its ligands, and it shows differential antagonistic activity towards EphA4 with different cognate ligand members. The antibody displays specificity on its antagonistic activity. IgG1 m105 binds EphA4 receptors on neurons upon stimulation by Aβ, the major agent causing synaptic impairment in AD. To the best knowledge of the present inventors, this is the first antagonistic EphA4 antibody. Although several earlier patent documents describe various EphA4 antibodies, none is similar to the fully human monoclonal antibodies of this invention. For example, U.S. Pat. No. 7,604,799 discloses EphA4 agonistic antibodies. However, these earlier antibodies are different from the antibodies of the present invention. Not only do they have different CDR amino acid sequences, these earlier antibodies also lack the high affinity binding EphA4 and the specificity of the antibodies of this invention. Similarly, the antibodies disclosed in U.S. Pat. No. 8,003,098 and 2009019121 A1 are not reported to have antagonistic activities.

II. Monoclonal Antibodies and Antigen Binding Fragments

The invention discloses novel anti-EphA4 antibodies. The antibodies and antigen binding fragments are disclosed herein that specifically bind EphA4, such as human and mouse EphA4. In some embodiments, antibodies bind EphA4 with a binding affinity of $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M.

In one embodiment, human EphA4 has the amino acid sequence set forth as

```
                                              (SEQ ID NO: 1)
MAGIFYFALF  SCLEGICDAV  TGSRVYPANE  VTLLDSRSVQ

GELGWIASPL  EGGWEEVSIM  DEKNTPIRTY  QVCNVMEPSQ
```

```
                      -continued
NNWLRTDWIT  REGAQRVYIE  IKFTLRDCNS  LPGVMGTCKE

TFNLYYYESD  NDKERFIREN  QFVKIDTIAA  DESFTQVDIG

DRIMKLNTEI  RDVGPLSKKG  FYLAFQDVGA  CIALVSVRVF

YKKEPLTVRN  LAQFPDTITG  ADTSSLVEVR  GSCVNNSEEK

DVPKMYCGAD  GEWLVPIGNC  LCNAGHEERS  GECQACKIGY

YKALSTDATC  AKCPPHSYSV  WEGATSCTCD  RGFFRADNDA

ASMPCTRPPS  APLNLISNVN  ETSVNIEWSS  PQNTGGRQDI

SYNVVCKKCG  AGDPSKCRPC  GSGVHYTPQQ  NGLKTTKVSI

TDLLAHTNYT  FEIWAVNGVS  KYNPNPDQSV  SVTVTTNQAA

PSSIALVQAK  EVTRYSVALA  WLEPDRPNGV  ILEYEVKYYE

KDQNERSYRI  VRTAARNTDI  KGLNPLTSYV  FHVRARTAAG

YGDFSEPLEV  TTNTVPSRII  GDGANSTVLL  VSVEGSVVIV

VILIAAFVIS  RRRSKYSKAK  QEADEEKKIN  QGVRTYVDPF

TYEDPNQAVR  EFAKEIDASC  IKIEKVIGVG  EFGEVCSGRL

KVPGKREICV  AIKTLKAGYT  DKORRDFLSE  ASIMGQFDHP

NITHIEGVVT  KCKPVMTTTE  YMENGSLDAF  LRKNDGRFTV

IQLVGMLRGI  GSGMKYLSDM  SYVHRDLAAR  NILVNSNLVC

KVSDFGMSRV  LEDDPEAAYT  TRGGKIPIRW  TAPEAIAYRK

FTSASDVWSY  GIVMWEVMSY  GERPYWDMSN  QDVIKAIEEG

YRLPPPMDCP  IALHQLMIDC  WQKERSDRPK  FGQIVNMLDK

LIRNPNSLKR  TGTESSRPNT  ALLDPSSPEF  SAVVSVGDWL

QVIKMDRYKD  NFTAAGYTTL  EAVVEVNQE
```

See also GENEBANK Accession No. AAH26327.1, as available on Jul. 30, 2005, which is incorporated by reference herein.

In additional embodiments, mouse EphA4 has the amino acid sequence set forth as:

```
                                              (SEQ ID NO: 2)
MDEKNTPIRT  YQVCNVMEAS  QNNWIRTDWI  TREGAQRVYI

EIKFTLRDCN  SLPGVMGTCK  ETFNLYYYES  DNDKERFIRE

SQFGKIDTIA  ADESFTQVDI  GDRIMRLNTE  IRDVGPLSKK

GFYLAFQDVG  ACIALVSVRV  FYKKCPLTVR  NLAQFPDTIT

GADTSSLVEV  RGSCVNNSEE  KDVPKMYCGA  DGEWLVPIGN

CLCNAGHEEQ  NGECQACKIG  YYKALSTDAS  CAKCPPHSYS

VWEGATSCTC  DRGFFRADND  AASMPCTRPP  SAPLNIISNV

NETSVNLEWS  SPQNTGGRQD  ISYNVVCKKC  GAGDPSKCRP

CGSGVHYTPQ  QNGLKTTRVS  ITDLLAHTNY  TFEIWAVNEV

SKYNPSPDQS  VSVTVTTNQA  APSSIALVQA  KEVTRYSVAL

AWLEPDRPNG  VILEYEVKYY  EKDQNERSYR  IVRTAARNTD

TRGINPLTSY  VFHVRARTAA  GYGDFSEPLE  VTTNTVPSRT

IGDGANSTVL  LVSVSGSVVL  VVILIAAFVI  SRRRSKYSKA

KQEADEEKHL  NQGVRTYVDP  FTYEDPNQAV  REFAKEIDAS
```

-continued

```
CIKIEKVIGV GEFGEVCSGR LKVPGKREIC VAIKTLKAGY

TDKQRRDELS EASIMGQFDH PNIIHLEGVV TKCKPVMIIT

EYMENGSLDA ELRKYDGRFT VIQLVGMLRG IGSGMKYLSD

MSYVHRDLAA RNILVNSNLV CKVSDFGMSR VLEDDPEAAY

TTRGGKIPIR WTAPEAIAYR KFTSASDVNS YGIVMNEVMS

YGERPYWDMS NQDVIKAIEE GYPLPPPMDC PIALHQLMLD

CWQKERSDRP KEGQIVNMLD KLIRNPNSLK RTGSESSRPN

TALLDPSSPE FSAVVSVGDW LQAIKMDRYK DNFTAAGYTT

LFAVVHMSQD DLARIGITAI THQNKILSSV QAMRTQMQQM

HGRMVPV
```

See also GENEBANK Accession No. AAH04782, Oct. 3, 2003, which is incorporated by reference herein.

In some embodiments, the heavy chain variable domain of the antibody or antigen binding fragment includes one or more of the heavy chain CDRs of m101. The amino acid sequence of the heavy chain of m101 is:

```
(SEQ ID NO: 3, wherein the CDRs are indicated
with bold and underlining)
QVQLQQSGAEVKKPGSSVKVSCKASGYTFTGYYMHWVRQAPGQGLEW

MGGIIPIFGTANYAQKFQGRVTITADKSTSTAYMELSSLRSEDTAVY

YCATAPMVCSSTSCYLRGFDYWGQGTLVTVSS
```

Thus, in some embodiments the heavy chain variable domain of the antibody or antigen binding fragment includes one or more of amino acids 26-33 of the amino acid sequence set forth as SEQ ID NO:3, amino acids 51-58 of the amino acid sequence set forth as SEQ ID NO:3, and/or amino acids 97-115 of the amino acid sequence set forth as SEQ ID NO:3. In additional embodiments the heavy chain variable domain of the antibody or antigen binding fragment includes amino acids 26-33 of the amino acid sequence set forth as SEQ ID NO:3, amino acids 51-58 of the amino acid sequence set forth as SEQ ID NO:3, and amino acids 97-115 of the amino acid sequence set forth as SEQ ID NO:3. In further embodiments, the heavy chain variable domain of the antibody or antigen binding fragment includes the amino acid sequence set forth as SEQ ID NO:3. In all of these embodiments, the antibody specifically binds EphA4.

In additional embodiments, the heavy chain variable domain of the antibody or antigen binding fragment includes one or more of the heavy chain CDRs of m105. The amino acid sequence of the heavy chain of m105 is:

```
(SEQ ID NO: 4, wherein the CDRs are indicated
with bold and underlining)
EVQLVQSGAEVKKPGSSVKVSCKASGGTFSSYAISWVRQAPGQGLEW

MGGIIPIFGTANYAQKFQGRVTMTRDTSISTAYMELSRLRSDDTAVY

YCARELLYCSSTSCGTHGFDIWGQGTMVTVSS
```

Thus, in some embodiments the heavy chain variable domain of the antibody or antigen binding fragment includes one or more of amino acids 26-33 of the amino acid sequence set forth as SEQ ID NO:4, amino acids 51-58 of the amino acid sequence set forth as SEQ ID NO:4, and/or amino acids 97-115 of the amino acid sequence set forth as SEQ ID NO:4. In additional embodiments the heavy chain variable domain of the antibody or antigen binding fragment includes amino acids 26-33 of the amino acid sequence set forth as SEQ ID NO:4, amino acids 51-58 of SEQ ID NO:4, and amino acids 97-115 of the amino acid sequence set forth as SEQ ID NO:4. In further embodiments, the heavy chain variable domain of the antibody or antigen binding fragment includes the amino acid sequence set forth as SEQ ID NO:4. In all of these embodiments, the antibody specifically binds EphA4.

In additional embodiments, the heavy chain variable domain antibody or antigen binding fragment includes one or more of the heavy chain CDRs of m119. The amino acid sequence of the heavy chain of m119 is:

```
(SEQ ID NO: 5, wherein the CDRs are indicated
with bold and underlining)
EIVITQSPLSLPVTPGEPASISCRSSQSLLHGNGYNYLDWYLQKPGQ

SPQLLIYLGSNRASGVPDRFSGSGSGTDFTLKISRVEAEDVGVYYCM

QALQTPWTFGQGTKVEIK
```

Thus, in some embodiments the heavy chain variable domain of the antibody or antigen binding fragment includes one or more of amino acids 27-37 of the amino acid sequence set forth as SEQ ID NO:5, amino acids 55-57 of the amino acid sequence set forth as SEQ ID NO:5, and/or amino acids 94-100 of the amino acid sequence set forth as SEQ ID NO:5. In additional embodiments, the heavy chain variable domain of the antibody or antigen binding fragment includes embodiments the heavy chain of the antibody includes one or more of amino acids 27-37 of the amino acid sequence set forth as SEQ ID NO:5, amino acids 55-57 of the amino acid sequence set forth as SEQ ID NO:5, and amino acids 94-100 of the amino acid sequence set forth as SEQ ID NO:5. In further embodiments, the heavy chain variable domain of the antibody or antigen binding fragment includes the amino acid sequence set forth as SEQ ID NO:5. In all of these embodiments, the antibody specifically binds EphA4.

In some embodiments, the light chain variable domain of antibody or antigen binding fragment includes one or more of the light chain CDRs of m101. The amino acid sequence of the light chain of m101 is:

```
(SEQ ID NO: 6, wherein the CDRs are indicated
with bold and underlining)
DVVMTQSPLSLPVTPGEPASISCRSSQSLLHSNGYNYLDWYLQKPGQ

SPQLLIYLGSNRASGVPDRFSGSGSGTDFTLKISRVEAEDVGVYYCM

QALQTPITFGQGTRLEIK
```

Thus, the light chain variable domain of the antibody or antigen binding fragment can include one or more of amino acids 27-37 of the amino acid sequence set forth as SEQ ID NO:6, amino acids 55-57 of the amino acid sequence set forth as SEQ ID NO:6, and/or amino acids 94-100 of the amino acid sequence set forth as SEQ ID NO:6. In some embodiments, light chain variable domain of the antibody or antigen binding fragment includes amino acids 27-37 of the amino acid sequence set forth as SEQ ID NO:6, amino acids 55-57 of the amino acid sequence set forth as SEQ ID NO:6, and amino acids 94-100 of the amino acid sequence set forth as SEQ ID NO:6. In further embodiments, light chain variable domain of the antibody or antigen binding fragment includes the amino acid sequence set forth as SEQ ID NO:6. In all of these embodiments, the antibody specifically binds EphA4.

In some embodiments, the light chain variable domain of the antibody or antigen binding fragment includes one or more of the light chain CDRs of m105. The amino acid sequence of the light chain of m105 is:

(SEQ ID NO: 7, wherein the CDRs are indicated with bold and underlining)
DVVMTQSPLSLPVTPGEPASISCRSSQSLLHSNGYNYLDWYLQKPGQ

SPQLLIYLGSNRASGVPDRFSGSGSGTDFTLKISRVEAEDVGVYYCM

QALQTPLAFGGGTKVEIK

Thus, the light chain variable domain of the antibody or antigen binding fragment can include one or more of amino acids 27-37 of the amino acid sequence set forth as SEQ ID NO:7, amino acids 55-57 of the amino acid sequence set forth as SEQ ID NO:7, and/or amino acids 94-100 of the amino acid sequence set forth as SEQ ID NO:7. In some embodiments, the light chain variable domain of the antibody or antigen binding fragment includes amino acids 27-37 of the amino acid sequence set forth as SEQ ID NO:7, amino acids 55-57 of the amino acid sequence set forth as SEQ ID NO:7, and amino acids 94-100 of the amino acid sequence set forth as SEQ ID NO:7. In further embodiments, light chain variable domain of the antibody or antigen binding fragment includes the amino acid sequence set forth as the amino acid sequence set forth as SEQ ID NO:7. In all of these embodiments, the antibody specifically binds EphA4.

In some embodiments, the light chain variable domain of the antibody or antigen binding fragment includes one or more of the light chain CDRs of m119. The amino acid sequence of the light chain of m105 is:

(SEQ ID NO: 8 wherein the CDRs are indicated with bold and underlining)
EIVLTQSPLSLPVTPGEPASISCRSSQSLLHGNGYNYLDWYLQKPGQ

SPQLLIYLGSNRASGVPDRFSGSGSGTDFTLKISRVEAEDVGVYYCM

QALQTPWTFGQGTKVEIK

Thus, the light chain variable domain of the antibody or antigen binding fragment can include one or more of amino acids 27-37 of the amino acid sequence set forth as SEQ ID NO: 8, amino acids 55-57 of the amino acid sequence set forth as SEQ ID NO: 8, and/or amino acids 94-100 of the amino acid sequence set forth as SEQ ID NO: 8. In some embodiments, light chain variable domain of the antibody or antigen binding fragment includes amino acids 27-37 of the amino acid sequence set forth as SEQ ID NO:8, amino acids 55-57 of the amino acid sequence set forth as SEQ ID NO:8, and amino acids 94-100 of the amino acid sequence set forth as SEQ ID NO:8. In further embodiments, the light chain variable domain of the antibody or antigen binding fragment includes the amino acid sequence set forth as SEQ ID NO:8. In all of these embodiments, the antibody specifically binds EphA4.

The monoclonal antibodies, antigen binding fragments and bispecific antibodies disclosed herein can be fully human. Fully human monoclonal antibodies include a human framework region. The heavy chain framework regions can be one or more of the framework regions in SEQ ID NO:3, SEQ ID NO:4 or SEQ ID NO:5 (these sequences include CDR sequences as well as framework sequences). However, the heavy chain framework regions can be from another source. The light chain framework regions can be one or more of the framework regions set forth in SEQ ID NO:6, SEQ ID NO:7 or SEQ ID NO:8. However, the light chain framework regions can be from another source. In some embodiments the use of human framework regions reduces a response to an antibody when it is used therapeutically. Chimeric forms of the disclosed antibodies are also provided wherein one or more of the heavy chain framework regions and/or the light chain framework regions are from another species, such as a mouse, rat or rabbit antibody. In some embodiments, framework regions are selected that have low immunogenicity.

Any of heavy chain variable domain disclosed herein can be combined with any light chain variable domain region disclosed herein, provided the monoclonal antibody or an antigen binding fragment thereof specifically binds EphA4. In some embodiments, the monoclonal antibody or antigen binding fragment includes one of:

a) a heavy chain variable domain including amino acids 26-33 of the amino acid sequence set forth as SEQ ID NO:3, amino acids 51-58 of the amino acid sequence set forth as SEQ ID NO:3, and/or amino acids 97-115 of the amino acid sequence set forth as SEQ ID NO:3 and a light chain variable domain including amino acids 27-37 of the amino acid sequence set forth as SEQ ID NO:6, amino acids 55-57 of the amino acid sequence set forth as SEQ ID NO:6, and/or amino acids 94-100 of the amino acid sequence set forth as SEQ ID NO:6;

b) a heavy chain variable domain including amino acids 26-33 of the amino acid sequence set forth as SEQ ID NO:4, amino acids 51-58 of the amino acid sequence set forth as SEQ ID NO:4, and/or amino acids 97-115 of the amino acid sequence set forth as SEQ ID NO:4 and a light chain variable domain including amino acids 27-37 of SEQ ID NO:7, amino acids 55-57 of the amino acid sequence set forth as SEQ ID NO:7, and/or amino acids 94-100 of the amino acid sequence set forth as SEQ ID NO:7; or c) a heavy chain variable domain including amino acids 27-37 of the amino acid sequence set forth as SEQ ID NO:5, amino acids 55-57 of the amino acid sequence set forth as SEQ ID NO:5, and/or amino acids 94-100 of the amino acid sequence set forth as SEQ ID NO:5 and a light chain variable domain including amino acids 27-37 of the amino acid sequence set forth as SEQ ID NO:8, amino acids 55-57 of the amino acid sequence set forth as SEQ ID NO:8, and/or amino acids 94-100 of the amino acid sequence set forth as SEQ ID NO:8.

In other embodiments, the monoclonal antibody or antigen binding fragment includes one of:

a) a heavy chain variable domain including amino acids 26-33 of the amino acid sequence set forth as SEQ ID NO:3, amino acids 51-58 of the amino acid sequence set forth as SEQ ID NO:3, and amino acids 97-115 of the amino acid sequence set forth as SEQ ID NO:3 and a light chain variable domain including amino acids 27-37 of the amino acid sequence set forth as SEQ ID NO:6, amino acids 55-57 of SEQ ID NO:6, and amino acids 94-100 of the amino acid sequence set forth as SEQ ID NO:6;

b) a heavy chain variable domain including amino acids 26-33 of the amino acid sequence set forth as SEQ ID NO:4, amino acids 51-58 of the amino acid sequence set forth as SEQ ID NO:4, and amino acids 97-115 of the amino acid sequence set forth as SEQ ID NO:4 and a light chain variable domain including amino acids 27-37 of the amino acid sequence set forth as SEQ ID NO:7, amino acids 55-57 of SEQ ID NO:7, and amino acids 94-100 of the amino acid sequence set forth as SEQ ID NO:7; or c) a heavy chain variable domain including amino acids 27-37 of the amino acid sequence set forth as SEQ ID NO:5, amino acids 55-57 of the amino acid sequence set forth as SEQ ID NO:5, and amino acids 94-100 of the amino acid sequence set forth as SEQ ID NO:5 and a light chain variable domain including amino acids 27-37 of the amino acid sequence set forth as SEQ ID NO:8, amino acids 55-57 of SEQ ID NO:8, and amino acids 94-100 of the amino acid sequence set forth as SEQ ID NO:8.

In some embodiments, the monoclonal antibody or antigen binding fragment includes one of:

a) a heavy chain variable domain the amino acid sequence set forth as SEQ ID NO:3 and a light chain variable domain including the amino acid sequence set forth as SEQ ID NO:6;

b) a heavy chain variable domain the amino acid sequence set forth as SEQ ID NO:4 and a light chain variable domain including the amino acid sequence set forth as SEQ ID NO:7; or c) a heavy chain variable domain including the amino acid sequence set forth as SEQ ID NO:5 and a light chain variable domain including the amino acid sequence set forth as SEQ ID NO:8.

The monoclonal antibodies disclosed herein can be of any isotype. The monoclonal antibody can be, for example, an IgM or an IgG antibody, such as $IgG_1$, $IgG_2$, $IgG_3$ or an $IgG_4$. The class of an antibody that specifically binds EphA4 can be switched with another (for example, IgG can be switched to IgM), according to well-known procedures. Class switching can also be used to convert one IgG subclass to another, such as from $IgG_1$ to $IgG_2$.

Antibody fragments are encompassed by the present disclosure, such as Fab, F(ab')$_2$, and Fv which include a heavy chain and light chain variable region and are capable of binding the epitopic determinant on EphA4. These antibody fragments retain the ability to selectively bind with the antigen. The antigen binding fragments can be included in a bispecific antibody. These antigen binding fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of an scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m610.27. In one group of embodiments, the antibodies have $V_H$ CDRsm610.27, or a combination of these CDRs, as discussed above.

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochenm. Biophys.* 89:230, 1960; Porter, Biochenm. J. 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art (see above). Thus, one of skill in the art can readily review the sequences shown above, identify a conservative substitution, and produce the conservative variant using well-known molecular techniques.

Bispecific antibodies are also provided herein. One type of derivatized antibody is produced by crosslinking two (or more) different antibodies, antigen binding fragments, and/or engineered antibody domains eAds to create bispecific antibodies. Suitable cross-linkers include those that are heterobifunctional, having two distinctly reactive groups separated by an appropriate spacer (such as m-maleimido-benzoyl-N-hydroxysuccinimide ester) or homobifunctional (such as disuccinimidyl suberate). Such linkers are available from Pierce Chemical Company, Rockford, Ill. Thus, two of the disclosed EphA antibodies or antigen binding fragments thereof can be combined to form a bispecific antibody. The disclosed antibodies and antigen binding fragments also can be combined with an eAd to produce a bispecific antibody.

Conjugates of the disclosed monoclonal antibodies, antigen binding fragments and bispecific antibodies are provided herein. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule. Alternatively, the antibody, antigen binding fragment or bispecific antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the monoclonal antibody, antigen binding fragment or bispecific antibody and the effector molecule are polypeptides, the linkers may be joined to the constituent amino acids through their side groups (such as through a disulfide linkage to cysteine) or to the alpha carbon amino and carboxyl groups of the terminal amino acids. In fact, similar methods can be used to form a bispecific antibody, or multivalent antibody, such as by attaching a monoclonal antibody or antigen binding fragment to another antibody of interest.

The monoclonal antibodies, antibody fragments and bispecific antibodies disclosed herein that specifically bind EphA4 can be derivatized for linkage to another molecule (such as another peptide or protein). In general, the antibodies or portion thereof is derivatized such that the binding to EphA4 is not affected adversely by the derivatization or labeling. The monoclonal antibody, antigen binding fragment or bispecific antibody can be functionally linked (by chemical coupling, genetic fusion, noncovalent association or otherwise) to one or more other molecular entities, such as another antibody (for example, to form a bispecific antibody), a detection agent, a pharmaceutical agent, a toxin, and/or a protein or peptide that can mediate associate of the antibody or antibody portion with another molecule (such as a streptavidin core region or a polyhistidine tag).

Both covalent and noncovalent attachment means may be used for attachment of an effector molecule. The procedure for attaching an effector molecule to a monoclonal antibody, antigen binding fragment, or bi-specific antibody varies according to the chemical structure of the effector. In some circumstances, it is desirable to free the effector molecule from the monoclonal antibody, antigen binding fragment, or bi-specific antibody when the immunoconjugate has reached its target site. Therefore, in these circumstances, immunoconjugates will comprise linkages that are cleavable in the vicinity of the target site. Cleavage of the linker to release the effector molecule from the monoclonal antibody, antigen binding fragment, or bi-specific antibody may be prompted by enzymatic activity or conditions to which the immunoconjugate is subjected either inside the target cell or in the vicinity of the target site. In view of the large number of methods that have been reported for attaching a variety of radiodiagnostic compounds, radiotherapeutic compounds, labels (such as enzymes or fluorescent molecules) drugs, toxins, and other agents, one skilled in the art will be able to determine a suitable method for attaching a given agent to an antibody or other polypeptide.

In several embodiments, the linker can include a spacer element, which, when present, increases the size of the linker such that the distance between the effector molecule or the detectable marker and the antibody (or antigen binding fragment) is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

A monoclonal antibody, antigen binding fragment or bispecific antibody that specifically binds EphA4 can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP), yellow fluorescent protein (YFP). A monoclonal antibody, antigen binding fragment or bispecific antibody can also be labeled with enzymes that are useful for detection, such as horseradish peroxidase, β-galactosidase, luciferase, alkaline phosphatase, glucose oxidase and the like. A detectable enzyme can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. A monoclonal antibody, antigen binding fragment or bispecific antibody may also be labeled with biotin, and detected through indirect measurement of avidin or streptavidin binding. It should be noted that the avidin itself can be labeled with an enzyme or a fluorescent label.

A monoclonal antibody, antigen binding fragment or bispecific antibody may be labeled with a magnetic agent, such as gadolinium. A monoclonal antibody, antigen binding fragment or bispecific antibody can also be labeled with lanthanides (such as europium and dysprosium), and manganese. Paramagnetic particles such as superparamagnetic iron oxide are also of use as labels. A monoclonal antibody, antigen binding fragment or bispecific antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

A monoclonal antibody, antigen binding fragment or bispecific antibody can also be labeled with a radiolabeled amino acid. The radiolabel may be used for both diagnostic and therapeutic purposes. For instance, the radiolabel may be used to detect EphA4 by x-ray, emission spectra, or other diagnostic techniques. Examples of labels for polypeptides include, but are not limited to, the following radioisotopes or radionuclides: $^3H$, $^{14}C$, $^{15}N$, $^{35}S$, $^{90}Y$, $^{99}Tc$, $^{111}In$, $^{125}I$, $^{131}I$. In some embodiments, these conjugates are of use for the treatment of a tumor, for example a breast carcinoma, esophageal cancer, non-small cell lung cancer, gastric cancer and pancreatic cancer. In other embodiments, these toxins are of use to treat amyotrophic lateral sclerosis.

The monoclonal antibodies, antigen binding fragment and bispecific antibodies can be conjugated to therapeutic agents, such as chemotherapeutic agents to make an antibody drug conjugate (ADC). In several embodiments, various chemotherapeutic agents can be conjugated to the provided antibodies to generate a conjugate. In some embodiments, these conjugates are of use for the treatment of a tumor, for example a breast carcinoma, esophageal cancer, non-small cell lung cancer, gastric cancer and pancreatic cancer.

Toxins can be employed with a monoclonal antibody, antigen binding fragment or bispecific antibody that specifically bind EphA4, and antigen binding fragment of these antibodies. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401). In some embodiments, these conjugates are of use for the treatment of a tumor, for example a breast carcinoma, esophageal cancer, non-small cell lung cancer, gastric cancer and pancreatic cancer. In other embodiments, these toxins are of use to treat amyotrophic lateral sclerosis.

Saporin is a toxin derived from *Saponaria officinalis* that disrupts protein synthesis by inactivating the 60S portion of the ribosomal complex (Stirpe et al., *Bio/Technology*, 10:405-412, 1992). However, the toxin has no mechanism for specific entry into cells, and therefore requires conjugation to an antibody (or antigen binding fragment) that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM 107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Act 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

In one embodiment, the toxin is *Pseudomonas* exotoxin (PE) (U.S. Pat. No. 5,602,095). As used herein, PE includes full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the provided antibodies can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; WO 99/51643; Pai et al., Proc. Natl. Acad. Sci. USA, 88:3358-3362, 1991; Kondo et al., J. Biol. Chem., 263:9470-9475, 1988; Pastan et al., Biochim. Biophys. Acta, 1333:C1-C6, 1997. In some examples, the PE is PE38.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., Blood 113(16): 3792-3800, 2009; Onda et al., Proc. Natl. Acad. Sci. USA, 105(32):11311-11316, 2008; WO 2007/016150, WO 2009/032954, and WO 2011/032022).

In some examples, the PE is a variant that is resistant to lysosomal degradation, such as PE-LR (Weldon et al., Blood 113(16):3792-3800, 2009; WO 2009/032954). In other examples, the PE is a variant designated PE-LR/6X (WO 2011/032022). In other examples, the PE is a variant designated PE-LR/8M (WO 2011/032022).

A monoclonal antibody, antigen binding fragment or bispecific antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

The average number of effector molecule or detectable marker moieties per antibody (or antigen binding fragment) in a conjugate can range, for example, from 1 to 20 moieties per antibody (or antigen binding fragment). For some conjugates, the average number of effector molecule or detectable marker moieties per antibody (or antigen binding fragment) may be limited by the number of attachment sites on the antibody (or antigen binding fragment). For example, where the attachment is a cysteine thiol, an antibody (or antigen binding fragment) may have only one or several cysteine thiol groups, or may have only one or several sufficiently reactive thiol groups through which a linker may be attached. In certain embodiments, the average number of effector molecule or detectable marker moieties per antibody (or antigen binding fragment) in a conjugate range from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. See, for example, U.S. Pat. No. 7,498,298 (herein incorporated by reference in its entirety). The average number of effector molecule or detectable marker moieties per antibody (or antigen binding fragment) in preparations of conjugates may be characterized by conventional means such as mass spectroscopy and, ELISA assay.

The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments (such as thioMab or thioFab prepared as disclosed in WO2006/034488).

III. Nucleic Acids and Host Cells

Nucleic acids encoding the amino acid sequences of the disclosed heavy and light chain variable domains are also provided herein. The nucleic acid molecule can be a cDNA. Recombinant nucleic acid molecules encoding the disclosed antibodies and antigen binding fragments can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same protein sequence. Thus, nucleic acid molecules encoding the disclosed antibodies and antigen binding fragments, and their components, conjugates, bispecific forms, and conjugates are provided herein.

Nucleic acid sequences encoding monoclonal antibodies, antigen binding fragments, conjugates and bispecific antibodies that specifically bind EphA4 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20): 1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding monoclonal antibodies, antigen binding fragments, conjugates and bispecific antibodies that specifically bind EphA4 can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody use is prepared by inserting the cDNA which encodes a variable region from an antibody into a vector which comprises the cDNA encoding an effector molecule (EM), such as an enzyme or label. The insertion is made so that the variable region and the EM are read in frame so that one continuous polypeptide is produced. Thus, the encoded polypeptide contains a functional Fv region and a functional EM region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds. In yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the monoclonal antibodies, antigen binding fragments, and/or bispecific antibodies that specifically bind EphA4 is isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the monoclonal antibodies, antigen binding fragments, conjugates and bispecific antibodies that specifically bind EphA4, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, labeled antibody, or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional (antigen binding) fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the antibody, labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the monoclonal antibodies, antigen binding fragments, conjugates and bispecific antibodies that specifically bind EphA4 that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-

2156, 1963, and Stewart et al., *Solid Phase Peptide Synthesis,* 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

VI. Compositions and Therapeutic Methods

Compositions are provided that include a therapeutically effective amount of one or more of the monoclonal antibodies, antigen binding fragments, bispecific antibodies and/or conjugates thereof that specifically bind EphA4 and a carrier. Compositions are provided that include a therapeutically effective amount of one or more nucleic acids encoding the monoclonal antibodies, antigen binding fragments, bispecific antibodies, and/or conjugates that specifically bind EphA4 in a carrier. The compositions can be prepared in unit dosage forms for administration to a subject, such as a subject with a tumor, a neurodegenerative disorder, or a mood disorder. The compositions can be formulated for sustained release.

In some embodiments, the subject has a tumor including malignant tumors. Any tumor that expresses especially overexpresses EphA4 can be treated using the antibodies, antigen binding fragments, bispecific antibodies and conjugates disclosed herein. The tumor can be, for example a breast carcinoma, esophageal cancer, non-small cell lung cancer, gastric cancer and pancreatic cancer.

In other embodiments, the subject has a neurodegenerative disorder such as Alzheimer's disease (AD), Parkinson's disease (PD), multiple sclerosis (MS), or amyotrophic lateral sclerosis (ALS). One example of such a disease is a motor neuron disease, such as a G12 diseases in the ICD-10 classification of the WHO. In some embodiments, the motor neuron disease is an anterior horn diseases. In additional embodiments, the motor neuron disease is amyotrophic lateral sclerosis (ALS) or spinal muscular atrophy (SMA). In other embodiments, the subject has an affective disorder such as depression.

In some cases, patients receiving administration of the therapeutic composition of this invention do not yet exhibit any definitive symptoms of the pertinent diseases; rather, they may be deemed to have an increased risk of developing such a disease at a later time due to, e.g., an abnormally high level of EphA4 expression (as determined by the diagnostic methods of this invention, for instance). In other words, the compositions described herein may be used for therapeutic purposes as well as for prophylactic purposes.

Without being bound by theory, in some embodiments, the antibodies, antigen binding fragments, bispecific antibodies and conjugates can bind to EphA4, such as human and/or mouse EphA4, and inhibit an activity of EphA4, such as tyrosine kinase activity. In some embodiments, the antibodies, antigen binding fragments, bispecific antibodies and conjugates block autophosphorylation of EphA4, leading to reduced cell signaling. In some embodiments, the cell is a motor neuron, such as in a subject with ALS. In other embodiments, the cell is a tumor cell, such as in a subject with cancer.

In some embodiments, the subject has ALS, which may be familial ALS or sporadic ALS. The subject can have limb-onset ALS or bulbar onset ALS. In other embodiments, the subject has AD. In some non-limiting example, the subject can have "late-onset" ALS or AD, which develops in individuals over the age of 60. Thus, the subject can be more than 60, 65, 70, 75, 80 or 85 years old. In other non-limiting examples, the subject can have "early onset" ALS or AD, which develops in subjects 60 years of age or younger. Thus the subject can be an adult subject of 18 to 60 years of age, such as a subject that is between 20, 25, 30, 35, 35, 40, 45, 50, 55 years of age and 60 years of age. The subject can be a young adult (e.g., 20 to 39 years old), or middle aged (e.g., 40-64 years old), or a senior (e.g., more than 65 years old). The subject also can be treated with RILUZOLE™ (Rilutek), or the antibody, antigen binding fragment, conjugate or bispecific antibody can be administered in the absence of treatment with RILUZOLE™ (Rilutek).

The amount and timing of administration are at the discretion of the treating physician to achieve the desired purposes. The monoclonal antibody that specifically binds EphA4, antigen binding fragment, bispecific antibody or conjugate can be formulated for systemic or local (such as intra-tumor) administration. In one example, pharmaceutical composition is formulated for parenteral administration, such as intravenous administration. In other examples, the pharmaceutical composition is formulated for intramuscular administration.

The compositions for administration can include a solution of the monoclonal antibody that specifically binds EphA4, antigen binding fragment, bispecific antibody or conjugate, or a nucleic acid encoding the monoclonal antibody that specifically binds EphA4, antigen binding fragment, bispecific antibody or conjugate, dissolved in a pharmaceutically acceptable carrier, such as an aqueous carrier. In some examples, the monoclonal antibody, antigen binding fragment, conjugate or bispecific antibody binds to EphA4 and interferes with signaling to improve survival, such as in a subject with ALS or a tumor. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

The monoclonal antibody that specifically binds EphA4, antigen binding fragment, bispecific antibody or conjugate can be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding a monoclonal antibody that specifically binds EphA4, antigen binding fragment, bispecific antibody or conjugate can also be administered to a subject. One approach to administration of nucleic acids is direct immunization with plasmid DNA, such as with a mammalian expression plasmid. The nucleotide sequence encoding the disclosed antibody can be placed under the control of a promoter to increase expression of the molecule. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding immunogenic peptides or other antigens to an organism. The methods include liposomal delivery of the nucleic acids.

In another approach to using nucleic acids can also be expressed by attenuated viral hosts or vectors or bacterial vectors. Recombinant vaccinia virus, adeno-associated virus (AAV), herpes virus, retrovirus, cytogmegalovirus, poxvirus or other viral vectors can be used to express the antibody. For example, vaccinia are described in U.S. Pat. No. 4,722,848. BCG (*Bacillus* Calmette Guerin) provides another vector for expression of the disclosed antibodies (see Stover, *Nature* 351:456-460, 1991).

In one embodiment, a nucleic acid encoding a disclosed monoclonal antibody that specifically binds EphA4, antigen binding fragment, bispecific antibody or conjugate is introduced directly into cells for expression. For example, the nucleic acid can be loaded onto gold microspheres by standard methods and introduced into the skin by a device such as Bio-Rad's Heliosä Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In one example, the subject is human. The antibody may be administered to a non-human mammal with a tumor expressing an EphA4 receptor with which the antibody, antigen binding fragment, conjugate, or bispecific antibody cross-reacts (such as a mouse, primate, or a cynomolgus or rhesus monkey). The antibody may also be administered to an animal that is a model system for ALS. It should be noted that animal models, such as mouse and primate models, can be useful for evaluating the mechanism of action and confirming the therapeutic efficacy of antibodies.

The monoclonal antibody that specifically binds EphA4, antigen binding fragment, bispecific antibody or conjugate, can be administered to a subject having a disease or disorders in which the presence of high levels of EphA4 receptor activity has been shown to be or is suspected of being either responsible for the pathophysiology of the disease or disorder or is a factor that contributes to a worsening of the disease or disorder. Accordingly, inhibition of EphA4 activity, or cells expressing the receptor, is expected to alleviate the symptoms and/or progression of the disorder. Such disorders may be evidenced, for example, by an increase in the levels of receptor for EphA4 on the cell surface or by increased amount of EphA4 in a subject suffering from the disorder.

The monoclonal antibody that specifically binds EphA4, antigen binding fragment, bispecific antibody or conjugate can slow or inhibit the growth of cells, such as tumor cells, either in vivo or in vitro. In the in vivo applications, a therapeutically effective amount of an antibody is administered to a subject in an amount sufficient to inhibit growth of a tumor, or to inhibit a sign or a symptom of the tumor. Suitable subjects may include those with a tumor that expresses the EphA4 receptor, such as those suffering from a breast carcinoma, esophageal cancer, non-small cell lung cancer, gastric cancer and pancreatic cancer. In some examples, the method causes the tumor not to increase in weight or volume or to decrease in weight or volume. In additional example, the method causes a reduction in metastasis.

The monoclonal antibody that specifically binds EphA4, antigen binding fragment, bispecific antibody or conjugate can be administered to a subject with a motor neuron disease, such as, but not limited to ALS, such as familial or sporadic ALS. Subjects of interest are disclosed above. The monoclonal antibody, antigen binding fragment, bispecific antibody or conjugate can be used to decrease the activity of EphA in motor neurons. In some embodiments, the progression of the disease is slowed. The monoclonal antibody can be used to determine the levels of EphA4 expression associated with ALS, or decreased EphA4 expression can be used to monitor response to therapy.

Typically, one or more symptoms or parameters will be evaluated to check the progression of the motor neuron disease in the subject. The treatment can reduce muscle weakness and/or atrophy. The treatment can decrease one or more symptoms such as difficulty moving, swallowing (dysphagia), and speaking or forming words (dysarthria). The treatment can also decrease tightness and stiffness of muscles (spasticity) and exaggerated reflexes (hyperreflexia), including reducing the gag reflex. The treatment can alter Babinski's sign (the large toe extends upward as the sole of the foot is stimulated), which indicates upper motor neuron damage is decreased. The treatment can delay or reduce motor neuron degeneration, and delay or reduce muscle weakness and atrophy, muscle cramps, and fleeting twitches of muscles that can be seen under the skin (fasciculations). The treatment can also reduce the pseudobulbar affect, also known as "emotional liability," thus reducing episodes of uncontrollable laughter, crying or smiling.

Amounts effective for this use will depend upon the severity of the disease and the general state of the patient's health. A therapeutically effective amount of the monoclonal antibody that specifically binds EphA4, antigen binding fragment, bispecific antibody or conjugate, or the nucleic acid encoding the monoclonal antibody that specifically binds EphA4, antigen binding fragment, bispecific antibody or conjugate, is that which provides either subjective relief of a symptom(s) or an objectively identifiable improvement as noted by the clinician or other qualified observer. In some embodiments, the treatment reduces cell signally, such as by decreasing the tyrosine kinase activity of EphA4 and/or autophosphorylation of EphA4.

The disclosed compositions can be administered in conjunction with another agent, such as an agent for the treatment of ALS, either simultaneously or sequentially. In specific non-liming examples, the subject has ALS, and another agent for the treatment of ALs is administered to the subject. In specific non-limiting examples, a therapeutically effective amount of RILUZOLE™ (Rilutek) is also administered.

For the treatment of a tumor, the disclosed composition can be administered with a chemotherapeutic agent. Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with the disclosed antibodies, antigen binding fragments and conjugates for the treatment of a tumor. Examples of useful COX-II inhibitors include CELEBREX™ (alecoxib), valdecoxib, and rofecoxib. Examples of useful matrix metalloproteinase inhibitors are described in WO 96/33172, WO 96/27583, WO 98/07697, WO 98/03516, WO 98/34918, WO 98/34915, WO 98/33768, WO 98/30566, European Patent Publication 606,046, European Patent Publication 931,788, WO 90/05719, WO 99/52910, WO 99/52889, WO 99/29667, U.S. Pat. Nos. 5,863,949, 5,861,510, and European Patent Publication 780,386. In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxaicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The disclosed monoclonal antibody that specifically binds EphA4, antigen binding fragment, bispecific antibody or conjugate, or a nucleic acid encoding the monoclonal antibody that specifically binds EphA4, antigen binding fragment, bispecific antibody or conjugate, can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in WO 95/19970, WO 98/14451, WO 98/02434, and U.S. Pat. No. 5,747,498 (issued May 5, 1998). EGFR-inhibiting agents also include, but are not limited to, the mAbs C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), Cl-1033 (Warner Lambert Parke Davis), Cl-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds EphA4. VEGF inhibitors are described in, for example in WO 99/24440, WO 95/21613, WO 99/61422, U.S. Pat. No. 5,834,504, WO 98/50356, U.S. Pat. Nos. 5,883,113, 5,886,020, 5,792,783, WO 99/10349, WO 97/32856, WO 97/22596, WO 98/54093, WO 98/02438, WO 99/16755, and WO 98/02437. Other examples of some specific VEGF inhibitors are IM862 (Cytran Inc.); anti-VEGF mAb of Genentech, Inc.; and angiozyme, a synthetic ribozyme from Ribozyme and Chiron. These and other VEGF inhibitors can be used in conjunction with an antibody that specifically binds EphA4.

ErbB2 receptor inhibitors, such as GW-282974 (Glaxo Wellcome), and the mAbs AR-209 (Aronex Pharmaceuticals Inc.) and 2B-1 (Chiron), can furthermore be combined with the disclosed antibodies, antigen binding fragments, bispecific antibodies and conjugates, for example those indicated in WO 98/02434, WO 99/35146, WO 99/35132, WO 98/02437, WO 97/13760, WO 95/19970 and U.S. Pat. No. 5,587,458.

Single or multiple administrations of the compositions are administered, such as to a subject with ALS or a tumor, depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody, antigen binding fragment, bispecific antibody or conjugate is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the compositions disclosed herein. Various degradable and non-degradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

V. Diagnostic Methods and Kits

A method is provided herein for the detection of EphA4 in vitro or in vivo. In one example, expression of EphA4 is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human.

In several embodiments, a method is provided for detecting a tumor or assessing the risk of developing a tumor such as a breast carcinoma, esophageal cancer, non-small cell lung cancer, gastric cancer and pancreatic cancer. A method is also provided for determining the prognosis of a subject with any of these malignancies. The subject can be any subject of interest, such as a subject suspected of having the tumor. Increased levels of EphA4 in the sample from the subject, as compared to a control, indicates that the subject has the tumor or has an increased risk of developing a tumor at a later time. In specific non-limiting examples, the sample is a blood, serum, plasma, sputum, or biopsy sample.

In other embodiments, a method is provide for detecting or assessing the risk of developing a neurodegenerative disorder such as Alzheimer's disease (AD), Parkinson's disease (PD), multiple sclerosis (MS), or amyotrophic lateral sclerosis (ALS). One example of such a disease is a motor neuron disease, such as G12 diseases in the ICD-10 classification of the WHO. In some embodiments, the motor neuron disease is an anterior horn disease. In additional embodiments, the motor neuron disease is amyotrophic lateral sclerosis (ALS) or spinal muscular atrophy (SMA). In other embodiments, the subject has an affective disorder such as depression. In additional embodiments, the motor neuron disease is spinal muscular atrophy (SMA). The subject can be any subject of interest, such as a subject suspected of suffering from or having an increased risk of developing a neurodegenerative disorder such as AD, PD, MS, or ALS. Increased levels of EphA4 in the sample from the subject, as compared to a control, indicates that the subject has or at an elevated risk of developing the disorder such as the motor neuron disease of ALS. In specific non-limiting examples, the sample includes neurons.

In further embodiments, methods are provided to determine onset or progression of a neurodegenerative disorder such as AD, PD, MS, or ALS in a subject, comprising determining EphA4 levels in a sample of the subject. According to further specific embodiments, decreased EphA4 levels and/or activity are indicative of delayed onset (in a subject at risk of developing a neurodegenerative disease) and/or increased survival and/or fewer symptoms. Increased EphA4 levels are indicative of early onset (in a subject at risk of developing a neurodegenerative disease) and/or decreased survival (or disease duration) and/or increased symptoms of the disease, such as AD, PD, MS, and ALS. The disease can be familial or sporadic. The same general methodology may be used to determine onset or progression of an affective disorder such as depression in a subject, comprising determining EphA4 level in a sample of the subject and comparing the level with a standard control or with a previously determined EphA4 level from the same type of sample. An increase from the standard control value or a previously measured value indicates onset or progression of the disease.

Methods are provided for detecting EphA4 in a biological sample, wherein the method includes contacting a biological sample with a monoclonal antibody that specifically binds EphA4 or an antigen binding fragment thereof under conditions conducive to the formation of an immune complex, and detecting the immune complex, to detect the EphA4 in the biological sample. In one example, the detection of increased EphA4 in the sample indicates that the subject has a malignancy. In another example, the detection of increased EphA4 in the sample indicates that the subject is prone to metastasis. In further examples, the tumor is breast carcinoma, esophageal cancer, non-small cell lung cancer, gastric cancer and pancreatic cancer.

The amount of EphA4 in the sample can be compared to a control. The control can be a reference standard or a sample from a subject without the tumor or the motor neuron disease, such as a healthy subject.

Whenever a positive diagnosis is made, e.g., a patient is determined to either suffer from a tumor, a neurodegenerative disorder, or a mood disorder or have an increased risk of developing a tumor, a neurodegenerative disorder, or a mood disorder, the patient may be subject to additional testing to confirm the finding based on EphA4 results. In some cases, the patient may be given appropriate treatment for his or her condition using one or more clinically approved therapeutic or prophylactic methods. In addition, the patient may be subject to follow-up testing and treatment for continued maintenance and long term monitoring.

In one embodiment, the monoclonal antibody that specifically binds EphA4 or antigen binding fragment is directly labeled with a detectable label. In another embodiment, the monoclonal antibody that specifically binds EphA4 or antigen binding fragment (the first antibody) is unlabeled and a second antibody or other molecule that can bind the monoclonal antibody that specifically binds EphA4 or antigen binding fragment is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the monoclonal antibody that specifically binds EphA4 or antigen binding fragment, and for the secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, EphA4 can be assayed in a biological sample by a competition immunoassay utilizing EphA4 standards labeled with a detectable substance and an unlabeled human antibody that specifically binds EphA4. In this assay, the biological sample, the labeled EphA4 standards and the monoclonal antibody that specifically binds EphA4 or antigen binding fragment that specifically bind EphA4 are combined and the amount of labeled EphA4 standard bound to the unlabeled antibody is determined. The amount of EphA4 in the biological sample is inversely proportional to the amount of labeled EphA4 standard bound to the monoclonal antibody that specifically binds EphA4 or antigen binding fragment that specifically binds EphA4. The EphA4 can be human or mouse EphA4, depending on the sample of interest.

The immunoassays and method disclosed herein can be used for a number of purposes. In one embodiment, the monoclonal antibody that specifically binds EphA4 or antigen binding fragment can be used to detect the production of EphA4 by cells in cell culture. In another embodiment, the antibody can be used to detect the amount of EphA4 in a biological sample. Increased expression of EphA4 is associated with several types of cancer, including a breast carcinoma, esophageal cancer, non-small cell lung cancer, gastric cancer and pancreatic cancer. Thus, as disclosed above, the level of EphA4 can be used to diagnose, or determine the prognosis of, breast carcinoma, esophageal cancer, non-small cell lung cancer, gastric cancer or pancreatic cancer in a subject. Increased expression of EphA4 is also known to be correlated with the presence and severity of a motor neuron disease, such as ALS. Thus, as disclosed above, the level of EphA4 in a sample from a subject can be used to diagnose, or determine the prognosis of, a subject with a motor neuron disorder, such as ALS.

In one embodiment, a kit is provided for detecting EphA4 in a biological sample, such as a blood sample or biopsy sample. Kits for detecting a polypeptide will typically comprise a monoclonal antibody that specifically binds EphA4 or antigen binding fragment such as any of the antibodies or antigen binding fragments disclosed herein. In some embodiments, an antibody fragment, such as an Fv fragment is included in the kit. For in vivo uses, the antibody can be a scFv fragment. In a further embodiment, the monoclonal antibody that specifically binds EphA4, antigen binding fragment, or bispecific antibody is labeled (for example, with a fluorescent, radioactive, or an enzymatic label).

In one embodiment, a kit includes instructional materials disclosing means of use of an antibody that specifically binds EphA4. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting EphA4 in a biological sample generally includes the steps of contacting the biological sample with an antibody that specifically reacts, under immunologically reactive conditions, to an EphA4 polypeptide, such as human or mouse EphA4. The antibody is allowed to specifically bind under immunologically reactive conditions to form an immune complex, and the presence of the immune complex (bound antibody) is detected directly or indirectly.

The monoclonal antibody that specifically binds EphA4, antigen binding fragment or bispecific antibody can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbant assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the antibodies, antigen binding fragments, or bispecific antibodies that specifically bind EphA4, as disclosed herein, can be used in these assays. Thus, the antibodies can be used in a conventional immunoassay, including, without limitation, an ELISA, an RIA, FACS, tissue immunohistochemistry, Western blot or immunoprecipitation.

EXAMPLES

The following examples are provided by way of illustration only and not by way of limitation. Those of skill in the art will readily recognize a variety of non-critical parameters that could be changed or modified to yield essentially the same or similar results.

EphA4, the receptor for ephrin, is over-expressed in a wide variety of human malignant tumors, including, but not limited to, gastric cancer and non-small cell lung carcinoma (NSCLC). EphA4 is associated with tumor growth, invasion, metastasis and angiogenesis. In addition, EphA4 has also been found to be associated with the neurodegenerative disease Amyotrophic lateral sclerosis (ALS), where a defective EphA4 gene allows ALS patients to live considerably longer than patients with an intact gene. The identification and characterization of several human monoclonal antibodies (mAbs) that bind to human EphA4 and mouse EphA4 is provided herein. These mAbs can be used as ALS and cancer therapeutics as naked mAbs, in bi-specific formats, and/or as antibody-drug conjugates.

Example 1: Expression and Purification of 5 Recombinant EphA4

To efficiently select antibodies from phage libraries, a purified recombinant antigen, in this case EphA4, is needed. To increase the immunogenicity of the EphA4 molecule, both the human and mouse EphA4 gene were fused with human IgG1 Fc. The human and mouse EphA4-Fc purified by protein G was >95% in purity on a polyacrylamide gel. The purified mouse EphA4-Fc fusion protein was used for panning of a naïve human Fab phage display library derived from healthy human blood.

Example 2: High-Affinity Binding of Fabs to Recombinant EphA4

Figure 2:
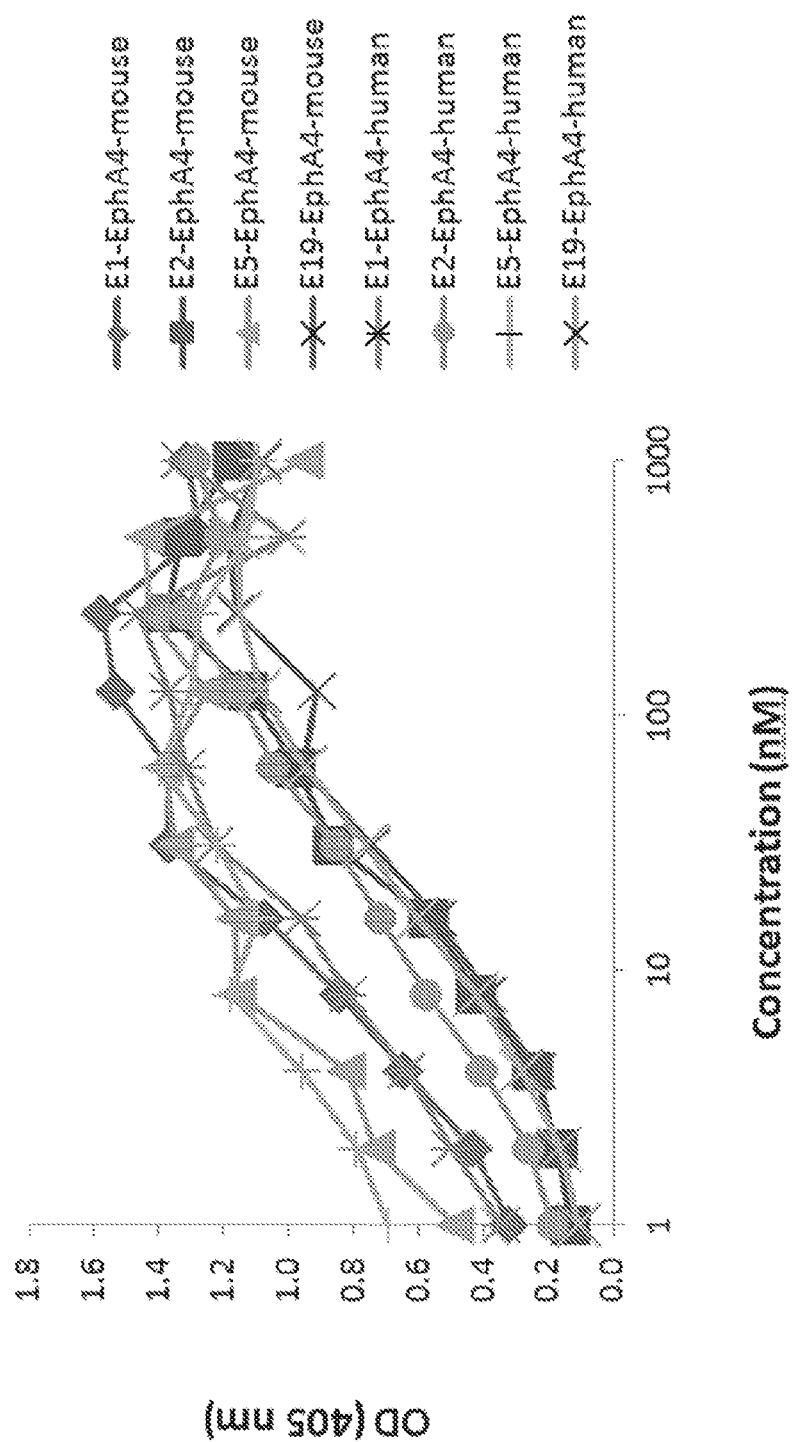
FIG. 2. Binding of IgG1s E1 (m101), E2, E5 (m105), and E19 (m119) to mouse and human EphA4 measured by ELISA. Serially diluted IgG1s were added to EphA4-coated wells. HRP-conjugated anti-FLAG Ab was used for detection.
Figure 3:
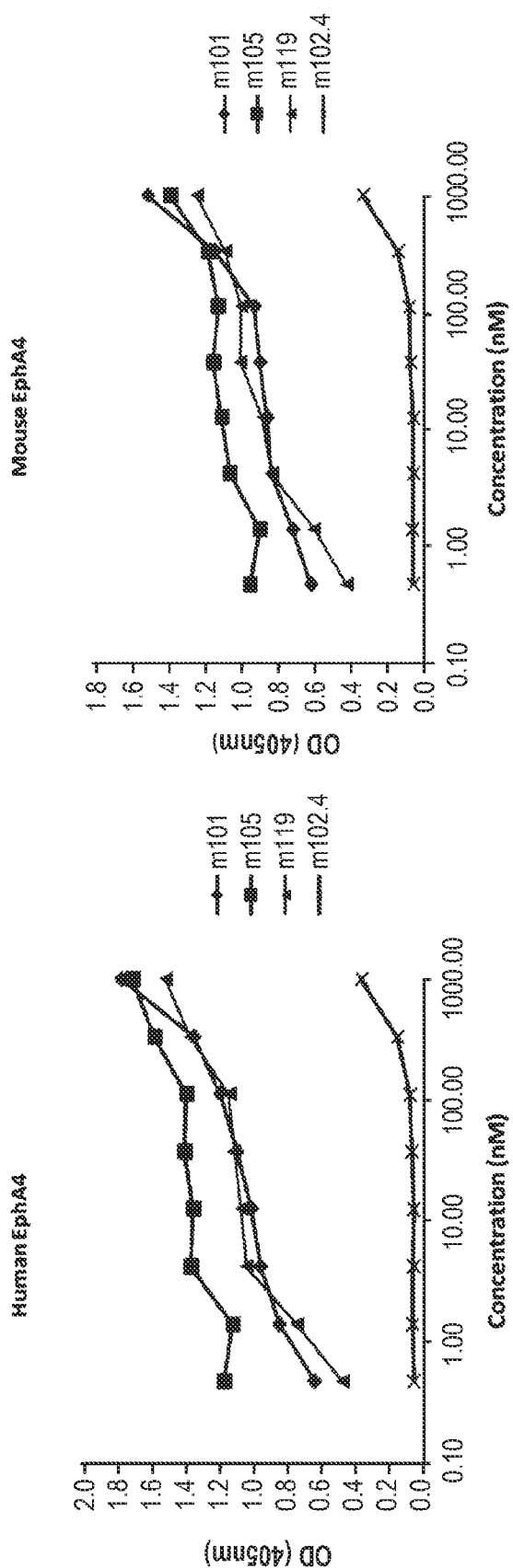
FIG. 3. Binding of IgG1s m101, m105, and m119 to mouse and human EphA4 measured by ELISA. Serially diluted IgG1s were added to EphA4-coated wells. HRP-conjugated anti-Fab Ab was used for detection.

The mouse EphA4-Fc produced in 293 Freestyle cells was labeled with biotin and used for panning of a large Fab library. After the third round of panning (FIG. 1), 200 clones were screened and tens of positive clones with different sequences were identified. Clones E1, E2, E5, and E19 bound with higher affinity to both human and mouse EphA4 than the other clones and were selected for further characterization. Fabs E1 (m101), E5 (m105) and E19 (m119) bound to human and mouse EphA4 with an EC50 of 5, 2, and 20 nmol/L as measured by ELISA (FIG. 2) were converted to IgG1 formats. The m101 and m119 IgG1s bound to human and mouse EphA4 with the same EC50 of 1 nmol/L, while the m105 IgG1 bound to human and mouse EphA4 with subnanomolar EC50 (FIG. 3).

Example 3: IgG1s m101, m105 and m119 Specifically Recognize the Ligand Binding Domain of EphA4

Figure 4:
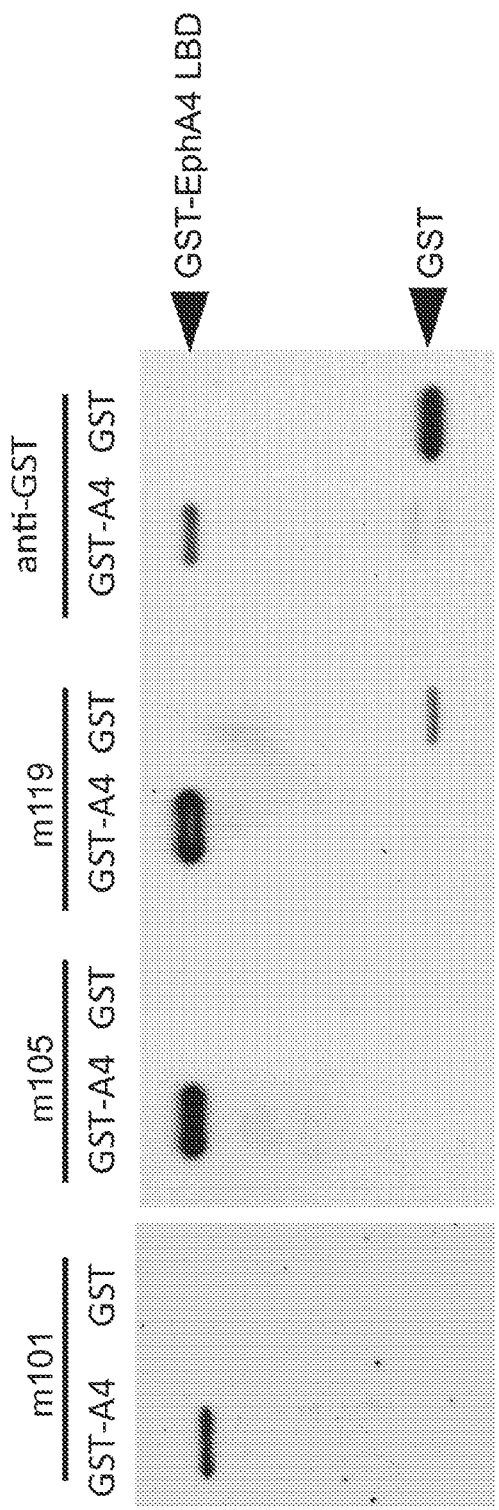
FIG. 4. IgG1s m101, m105, and m119 recognize human EphA4 ligand binding domain (LBD). The EphA4 LBD recombinant proteins were purified and subjected to western blot analysis using the indicated IgG1s.
Figure 5:
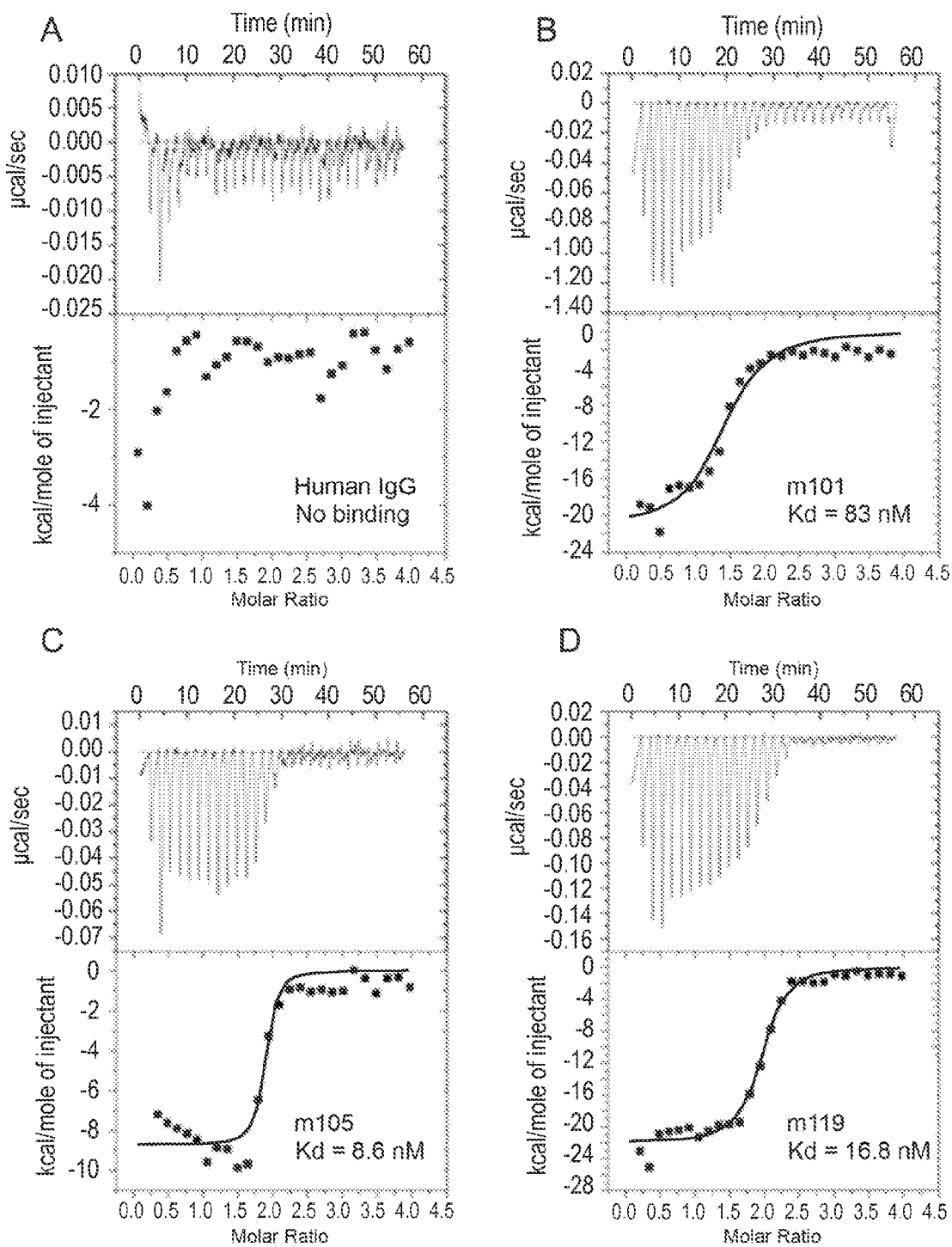
FIG. 5. IgG1s m101, m105, and m119 exhibit strong binding affinity towards the EphA4 LBD. Isothermal titration calorimetry (ITC) experiments were carried out by incubating 20 µM Eph LBD protein in the cell with 1 µM antibodies. (A) Human IgG showed no binding; (B) m101 showed binding affinity with Kd=~83.0 nM; (C) m105 showed strong binding affinity with Kd=~8.6 nM; (D) m119 showed binding affinity with Kd=~16.8 nM.

To investigate the binding property of the IgG1s m101, m105, and m119 to EphA4, GST-human EphA4 ligand binding domain (LBD) was expressed and purified. The recognition of EphA4 LBD by the 3 IgG1s m101, m105, and m119 was determined by Western blot analysis. The EphA4 LBD protein was run on SDS-PAGE and they were immunoblotted with the 3 IgG1s (FIG. 4). The kinetics of the 3 IgG1s and EphA4 LBD interaction were further analyzed by conducting isothermal titration calorimetry (ITC) experiments. The heat generated by the interaction of EphA4 LBD recombinant protein with the IgG1s was measured with a sensitive calorimeter. IgG1s m101, m105, and m119 exhibited strong binding affinity towards the EphA4 LBD (FIG. 5).

Example 4: IgG1s m101, m105 and m119 Attenuate the Interaction of Mouse Ephrin-A1 and Mouse EphA4

Figure 6:
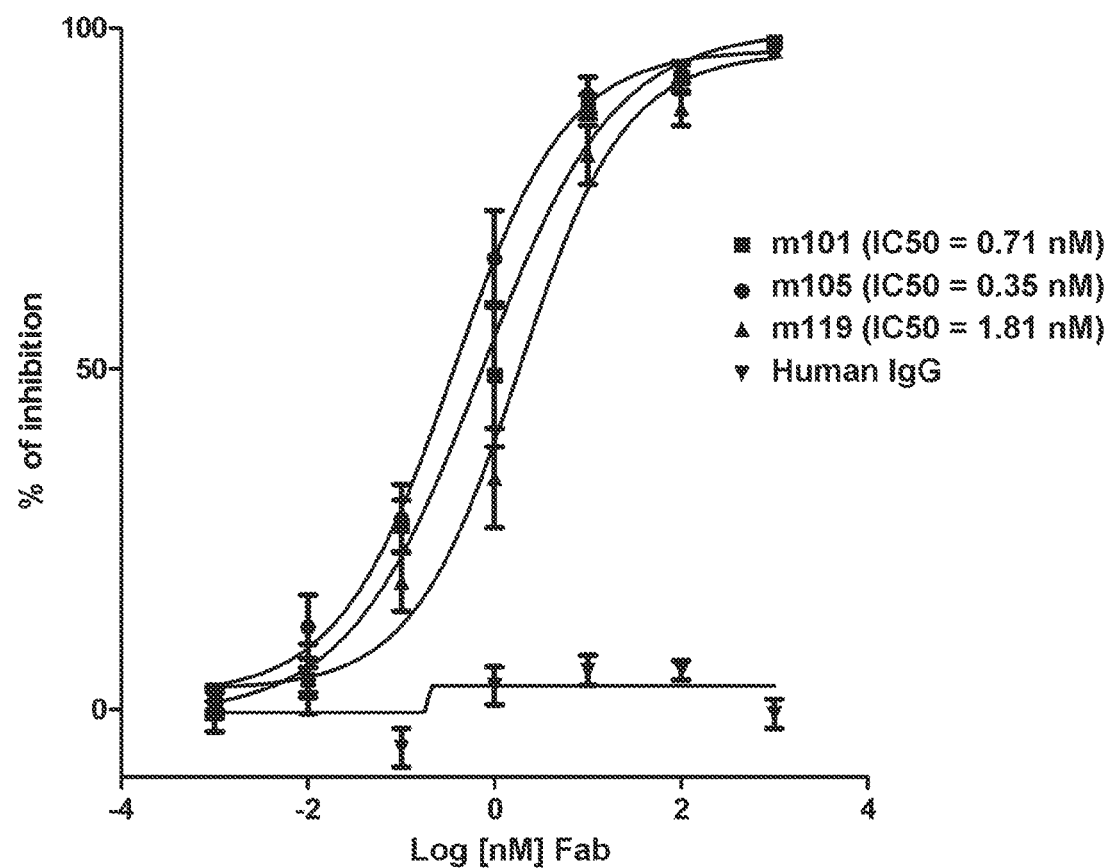
FIG. 6. IgG1s m101, m105, and m119 block the ephrin-A1/EphA4 interaction. The plot indicates that the 3 IgG1s were able to block the interaction between mouse EphA4 extracellular domain with mouse ephrin-A1, at a nano molar range (IC50: m101=0.71 nM; m105=0.35 nM; and m119=1.81 nM).

The competitive ELISA was performed to demonstrate both the binding of the IgGs towards EphA4 and inhibition against the interaction of EphA4 and its ligand ephrin-A. The ELISA plate was pre-coated with the extracellular domain of mouse EphA4 recombinant protein, and then incubated with IgG s m101, m105 or m119 at different concentrations, followed by several rounds of wash, and finally incubated with biotinylated recombinant mouse ephrin-A1 Fc chimeric protein. The interaction of EphA4 and ephrin-A that attenuated by the IgG1s was determined via the streptavidin-biotin detection method. IC50 of the 3 IgG1s were determined. As seen in FIG. 6, the 3 IgG1s were able to block the interaction between mouse EphA4 extracellular domain with mouse ephrin-A1, at a nanomolar range (IC50: m101=0.71 nM; m105=0.35 nM; and m119=1.81 nM).

Figure 7:
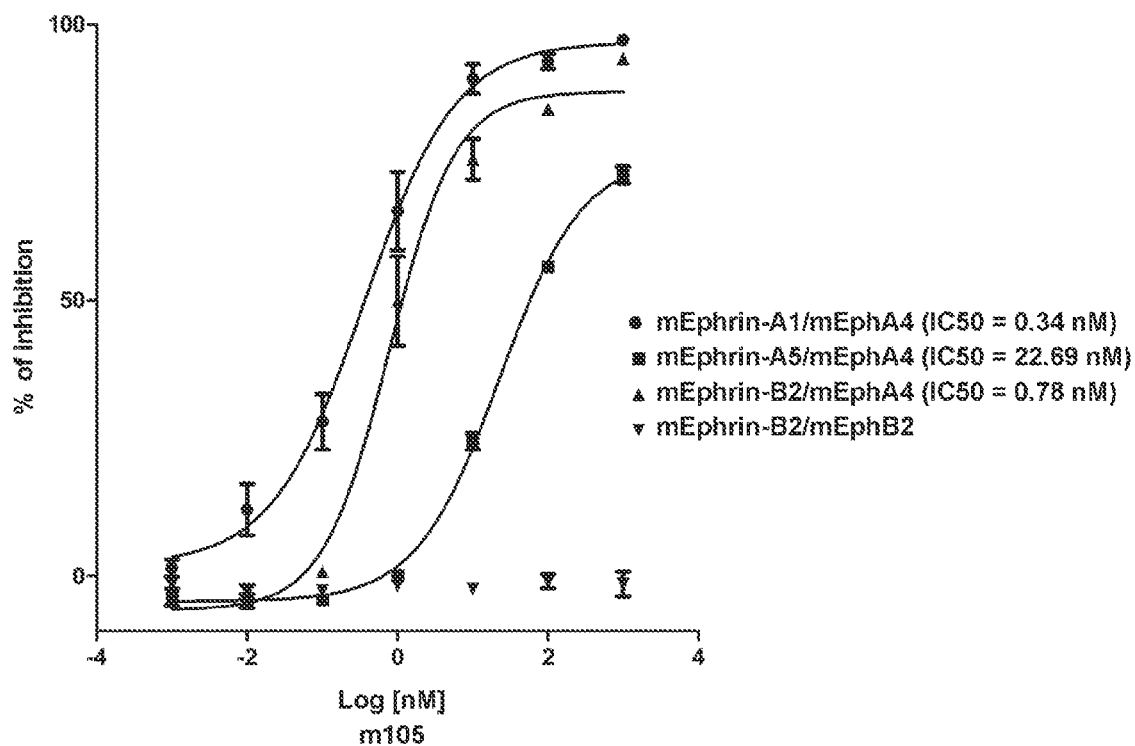
FIG. 7. IgG1 m105 shows specificity in blocking the EphA4-ligand interaction. The inhibition of mouse EphA4 with different ligands was indicated by the IC50 value (mEphrin-A1: 0.34 nM; mEphrin-A5: 22.69 nM; Ephrin-B2: 1.81 nM). m105 failed to recognize the mouse EphB2 and blocked its interaction with ephrin-B2.

Example 5: IgG1 m105 Specifically Attenuates Interaction of EphA4 with Ephrin-A/B but not Interaction Between Ephrin-B and EphB2 Receptor To determine the specificity of IgG1 m105 in attenuating EphA4 with its ligands, blocking the interaction of EphA4-ligands by IgG1 m105 was demonstrated by competitive ELISA. Extracellular domain of mouse EphA4 recombinant protein or extracellular domain of mouse EphB2 recombinant protein was first incubated with IgG1 m105, followed by incubating with different biotinylated recombinant mouse ephrin-A/ephrin-B Fc chimeric proteins. The effect of IgG1 m105 on the interaction of EphA4/EphB2 and ephrin-A/ephrin-B was then determined via the streptavidin-biotin detection method. As seen in FIG. 7, IgG1 m105 showed specificity in blocking EphA4 with ephrin-A and ephrin B.

Example 6: Specific Binding of mAbs to Cell Surface-Associated EphA4

Figure 8:
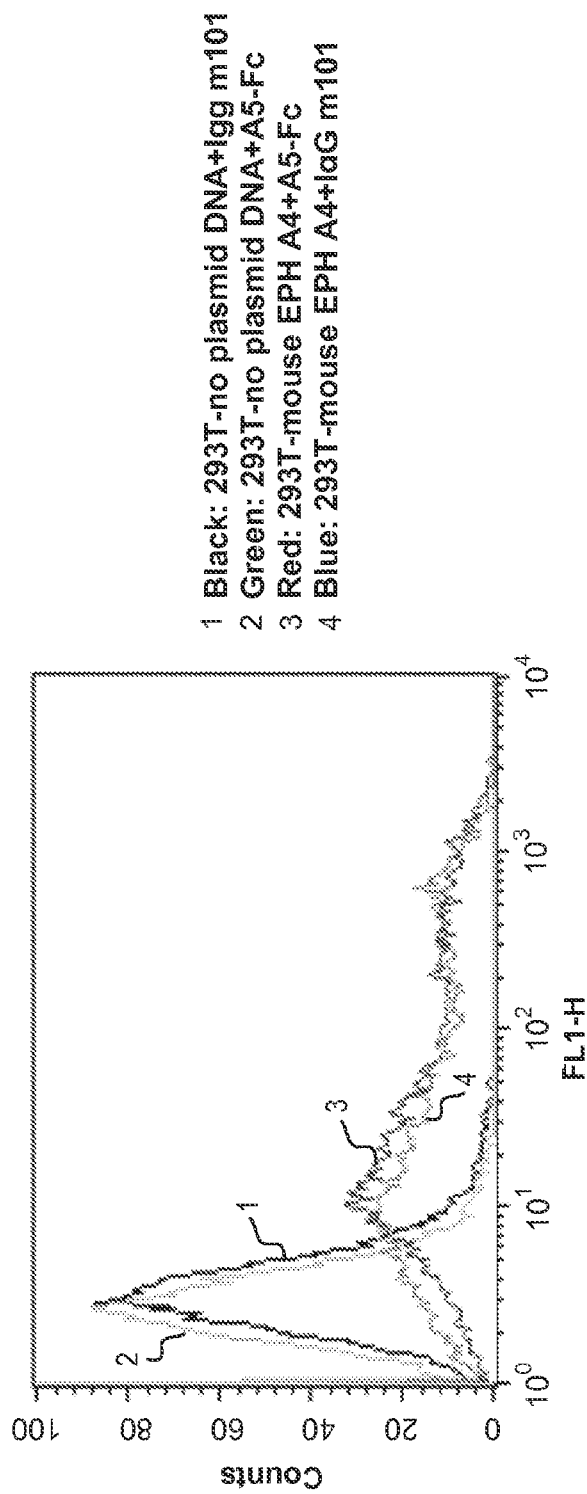
FIG. 8. Binding of IgG1 m101 to EphA4-expressing cells. 293T cells or 293T cells transfected with mouse EphA4 were incubated with IgG1 m101 or natural EphA4 ligand ephrin-A5-Fc. FITC-conjugated anti-human IgG Ab was used for detection.

A therapeutic or diagnostic antibody should recognize the native protein. Various clinical applications require different sizes and valences of antibodies for best effect. For example, small sizes are preferred for targeting and imaging, whereas full-size antibodies (IgGs) have a much longer half-life in circulation, and some are able to mediate effector functions. Therefore, IgG1 E1 (m101) was tested for binding to native EphA4 associated with cell surfaces. For these experiments, 293T cells were transiently transfected with mouse EphA4, and tested the binding of m101 to transfected cells as well as un-transfected cells. As indicated in FIG. 8, m101 bound specifically to EphA4-293T cells as potent as the nature ligand of EphA4, ephrin-A5-Fc, suggesting that the mAbs that were identified can specifically bind cell surface-associated EphA4.

Example 7: IgG1 m119 Stimulates EphA4 Activation

Figure 9:
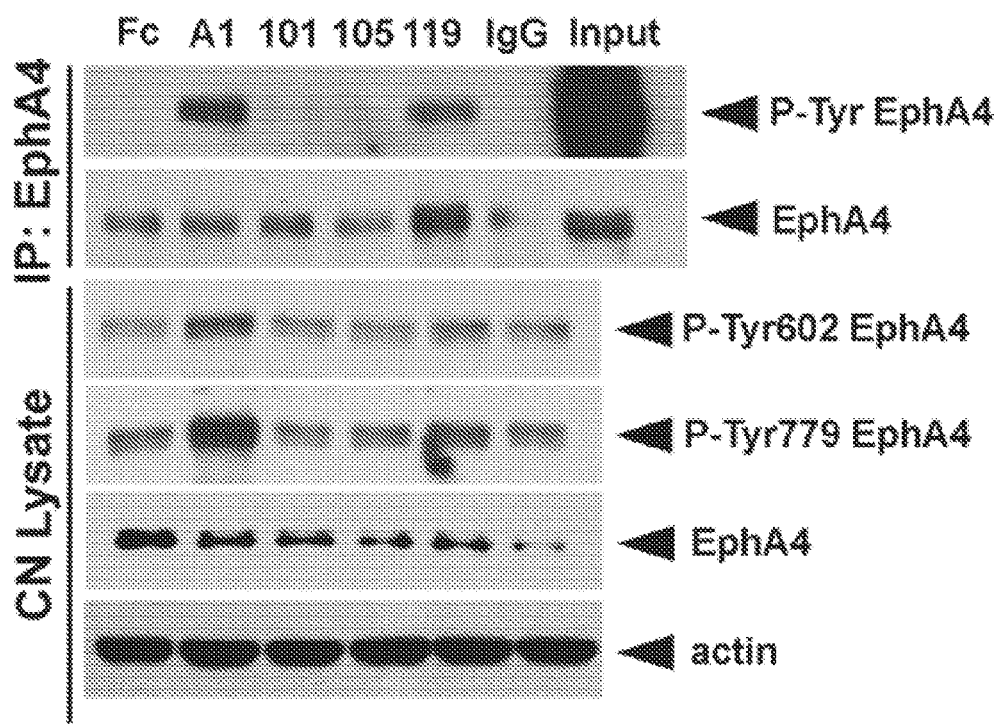
FIG. 9. IgG1 m119 induces the tyrosine phosphorylation of EphA4 in cultured cortical neurons. DIV 7 cortical neurons were treated with 2 µg/ml of m101 (101), m105 (105), m119 (119), and ephrin-A1 (A1) as positive control. The cells were harvested and subjected to immunoprecipitation and western blot analysis using the indicated antibodies.

IgG1s m101, m105, and m119 bind to the EphA4 and interfere with the interaction of EphA4 with ephrins. Their ability to act as agonists to regulate EphA4 activation in vivo was examined. The activation of EphA4 receptor by the IgG1s was determined by tyrosine phosphorylation of EphA4 in IgG1s-treated cultured cortical neurons. In brief, cultured cortical neurons were treated with the IgG1s m101, m105, or m119 at a concentration of 2 µg/ml. EphA4 protein was immunoprecipitated with EphA4 antibody from the protein lysates, run on SDS-PAGE, and then immunoblotted with tyrosine phosphorylated antibody (see FIG. 9).

Figure 10:
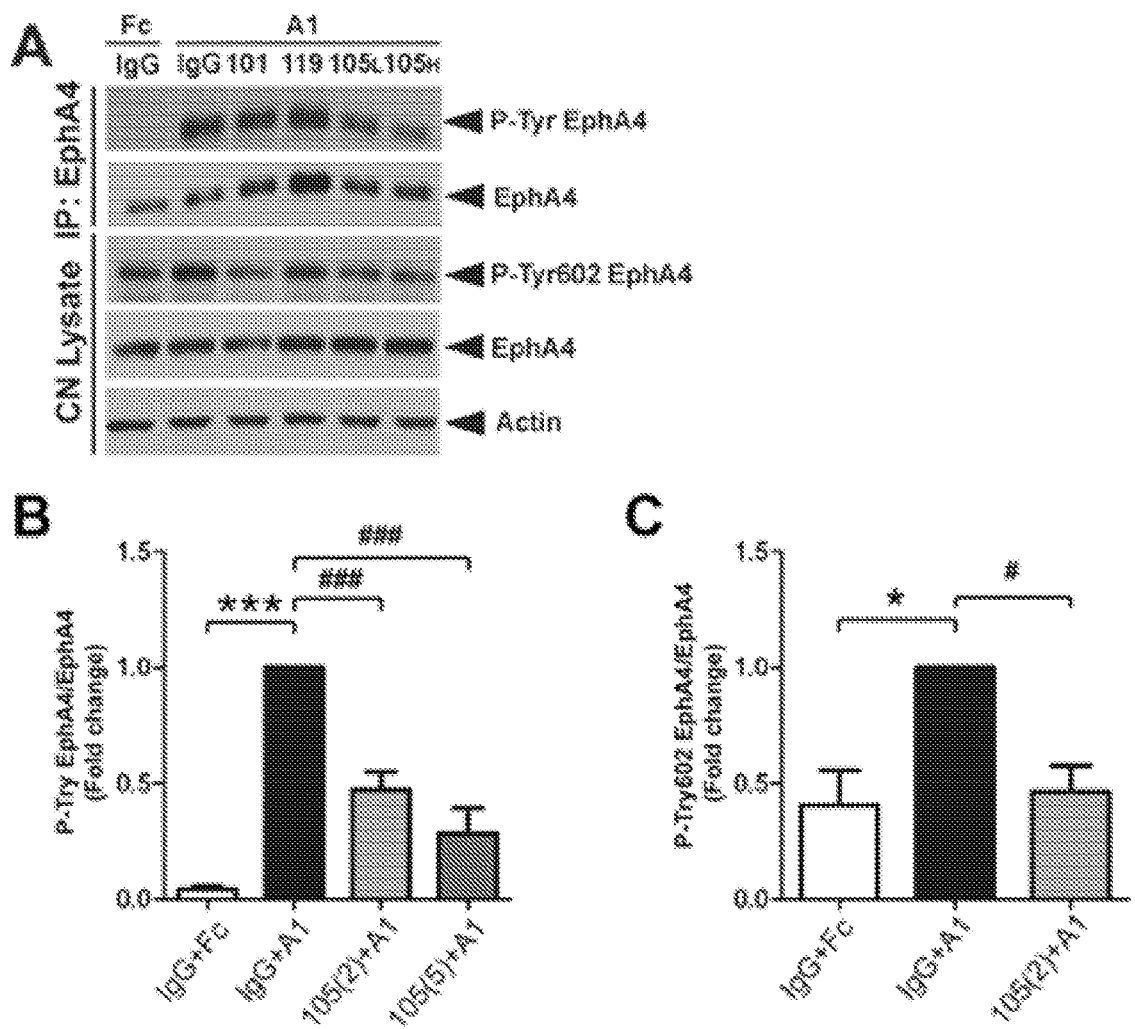
FIG. 10. IgG1 m105 inhibits the EphA4 activation induced by ephrin-A1. (A) m105 attenuates the ephrin-A1-induced phosphorylation of EphA4 in a dose-dependent manner. (B) Quantification of P-Tyr of EphA4 after immunoprecipitation; one-way ANOVA with post-hoc t-tests, ***$p<0.001$ vs. IgG+Fc; ###$p<0.001$ vs. IgG+A1. (C) Quantification of Tyr602 phosphorylation of EphA4; one-way ANOVA with post-hoc t-tests, *$p<0.05$ vs. IgG+Fc, #$p<0.05$ vs. IgG+A1.

Example 8: IgG1 m105 Acts as an EphA4 Antagonist that Attenuates the Ephrin-A1-Induced EphA4 Activation IgG1s m101, m105, and m119 bind to the EphA4 LBD and interfere with the interaction of EphA4 with ephrins. Their ability to act as antagonists to attenuate EphA4 activation was examined in cultured neurons. Cultured cortical neurons at 7 DIV were pretreated with indicated IgG1s before the treatment with pre-clustered ephrin-A1. For m105, this was 2 µg/ml for lower dose (indicated as 105L) and 5 µg/ml for higher dose (indicated as 105H), while m101 (101), 119 (119), and IgG were all at 5 µg/ml. The cells were then harvested and subjected to immunoprecipitation and western blot analysis using the indicated antibodies. As seen in FIG. 10(A), m105 attenuates the ephrin-A1-induced phosphorylation of EphA4 in a dose-dependent manner. The graphs show quantification of P-Tyr of EphA4 after immunoprecipitation (FIG. 10(B)) and quantification of Tyr602 phosphorylation of EphA4 (FIG. 10(C)).

Example 9: IgG1 m105 Recognizes EphA4 in Cultured Hippocampal Neurons: Aβ Reduces the Co-Localization of m105 Labeled EphA4 Receptors with Postsynaptic Marker PSD-95

Figure 11:
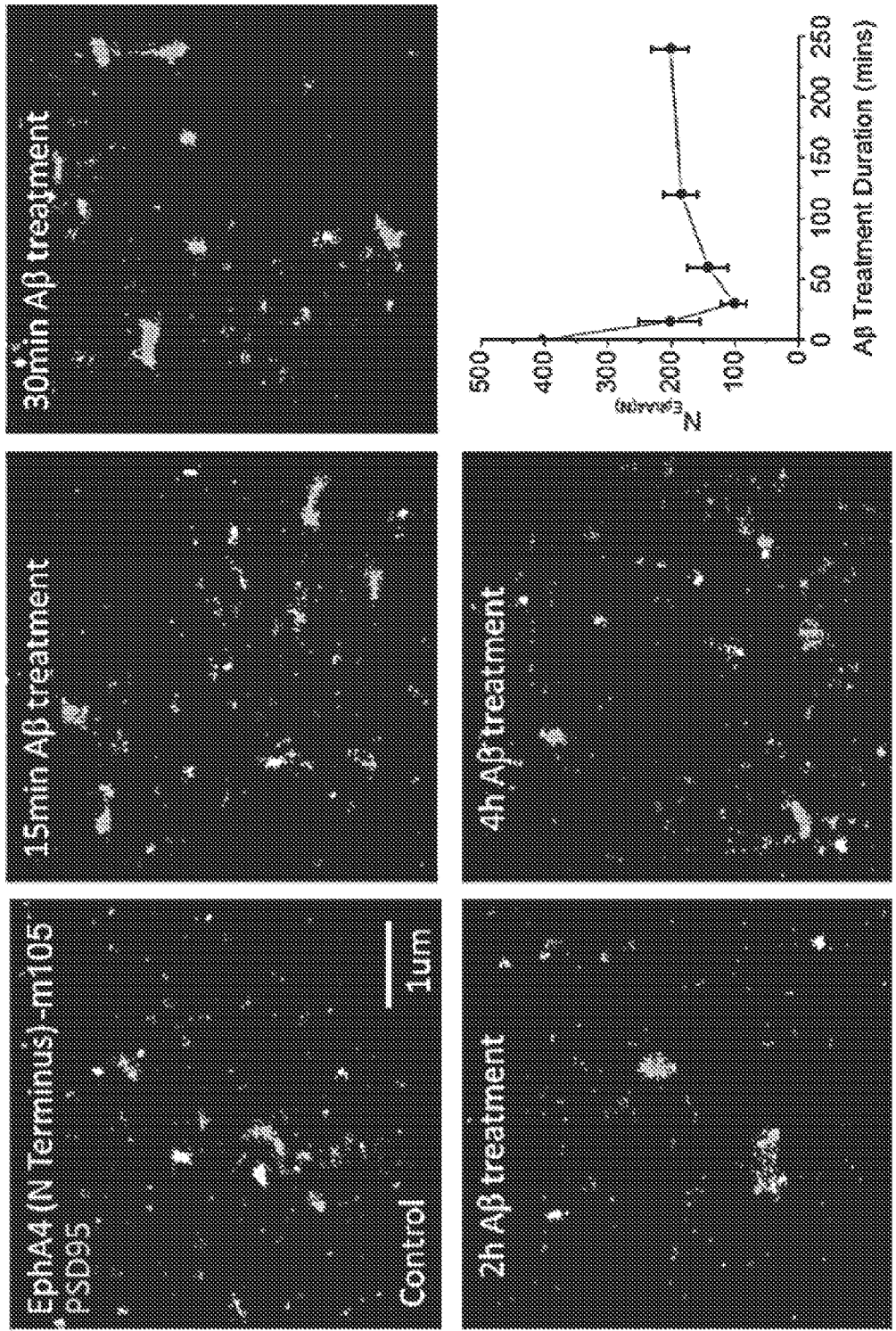
FIG. 11. Aβ reduces the co-localization of m105 labeled EphA4 receptors with PSD-95. Fluorescent images show the cultured hippocampal neurons (~18-20 DIV) treated with 500 nM Aβ at different time points, as indicated. The cells were immunostained with IgG1 m105 and PSD-95 antibody. The graph shows a decrease in EphA4 co-localized with PSD-95. NEphA4(n) represents the number of localizations (or the localization counts) via super-resolution imaging. This number reflects only the relative abundance of EphA4 (N) but it is not the exact number of proteins or even the number of fluorescent tags, since each dye molecule may switch many times during imaging.

As shown in FIG. 11. Aβ reduces the co-localization of m105 labeled EphA4 receptors with PSD-95. Fluorescent images show the cultured hippocampal neurons (~18-20 DIV) treated with 500 nM A3 at different time points, as indicated. The cells were immunostained with IgG1 m105 and PSD-95 antibody. The graph shows decreased level of EphA4 co-localized with PSD-95. NEphA4(n) represents the number of localizations (or the localization counts) in super-resolution imaging. This number reflects only the relative abundance of EphA4(N) but it is not the exact number of proteins, or even the number of fluorescent tags since each dye molecule may switch many times during imaging.

Figure 12:
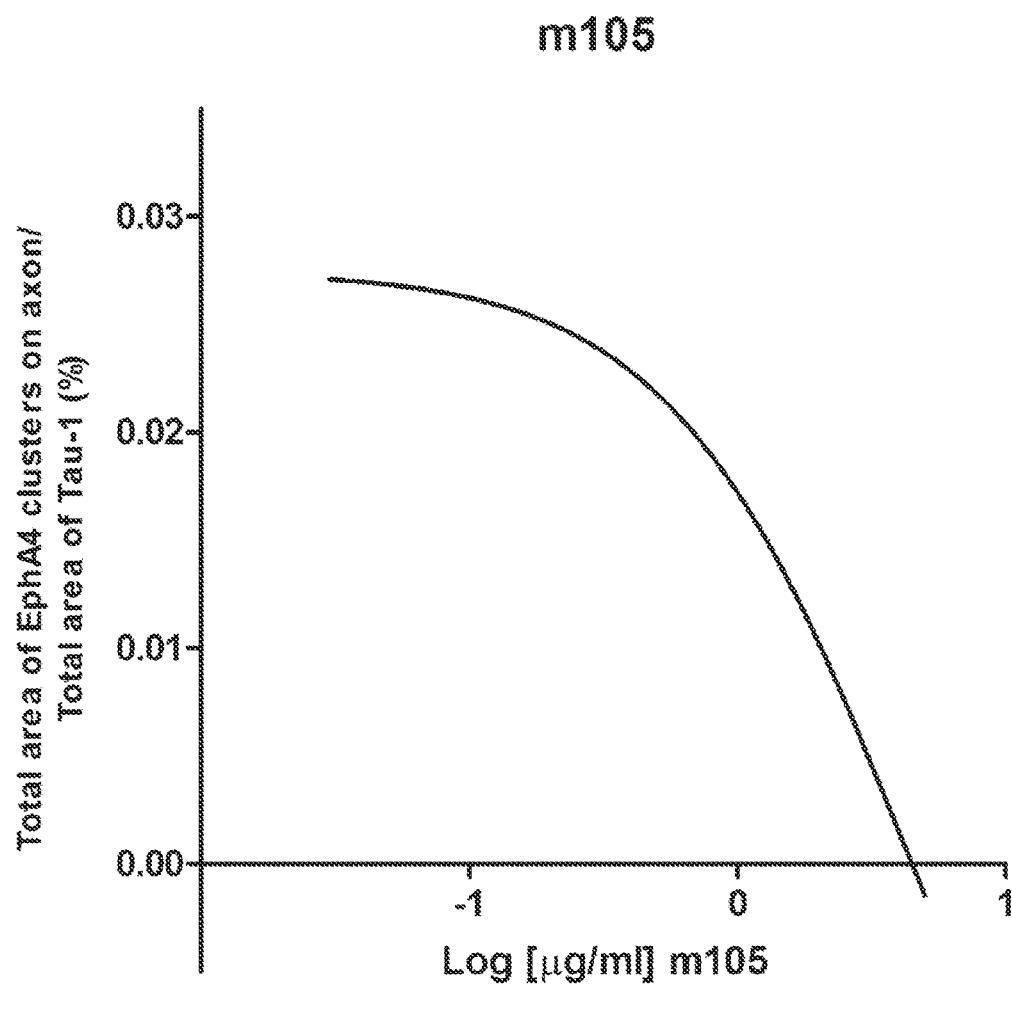
FIG. 12. m105 inhibits the biological function of EphA4-mediated signaling. m105 abolishes ephrin-A1-induced EphA4 clustering in cultured hippocampal neurons in a dose-dependent manner. The IC50 of m105 in inhibiting Ehrin-A1 mediated EphA4 clusters was 4.16 µg/ml.

Example 10: Blockade of EphA4 Forward Signaling Rescues Aβ$_{(1-42)}$ Oligomer-Mediated Impairment of Synaptic Transmission To examine the ability of IgG1 m105 in inhibiting EphA4 signaling, EphA4 clustering assay was performed. As shown in FIG. 12, EphA4 clusters were quantified by calculating the proportion of total area of EphA4 clusters on axons (Tau positive area).

Figure 13:
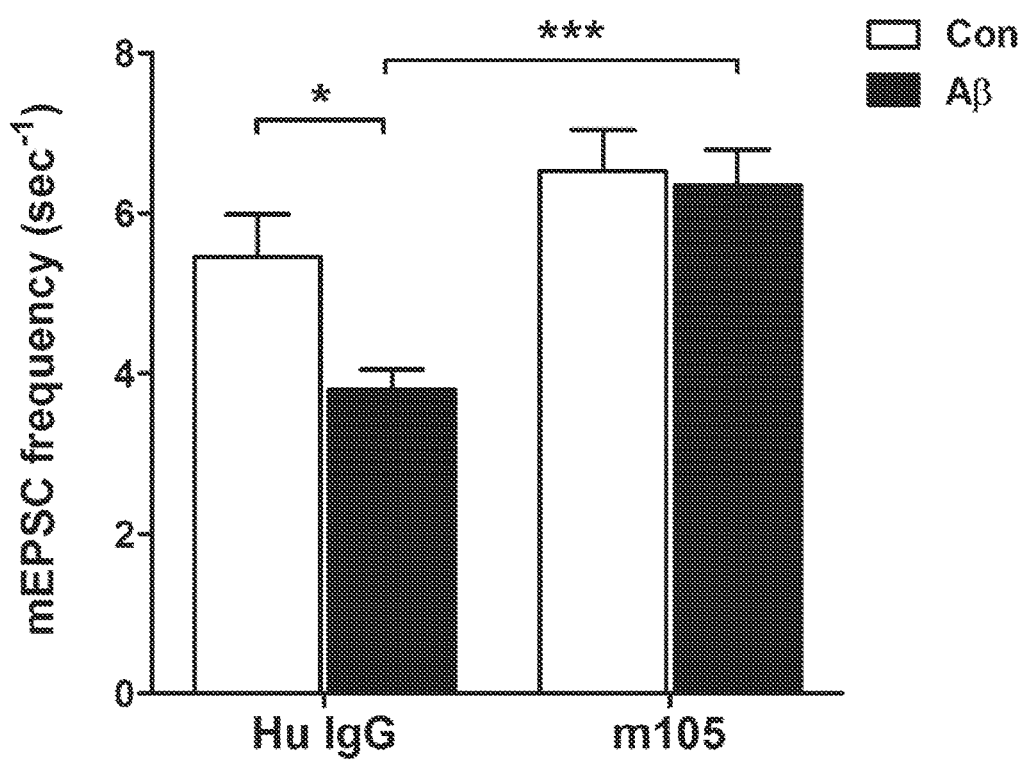
FIG. 13. Blockade of EphA4 signaling by m105 antibody rescues the $Aβ_{(1-42)}$ oligomer-mediated impairment of neurotransmission. m105 antibody, which blocks the interaction of endogenous EphA4 and ephrin-A, rescues the $Aβ_{(1-42)}$ oligomer (500 nM)-mediated reduction of frequency of mEPSC. Cultured hippocampal neurons (22 DIV) were treated with 2 µg/ml m105 for 30 min prior 500 nM $Aβ_{(1-42)}$ for 24 hr.

Blockade of EphA4 forward signaling rescues Aβ$_{(1-42)}$ oligomer-mediated impairment of synaptic transmission and synaptic plasticity. As seen in FIG. 13, m105 antibody, which blocks the interaction of endogenous EphA4 and ephrin-A, rescues the Aβ$_{(1-42)}$ oligomer (500 nM)-mediated reduction of frequency of mEPSC. Cultured hippocampal neurons (22 DIV) were treated with 2 µg/ml m105 for 30 min prior 500 nM Aβ(1-42) for 24 hr.

Material and Methods

Production of EphA4 Proteins.

The human and mouse EphA4 gene segments were synthesized by Genscript (Piscataway, N.J.). The plasmids encoding human or mouse EphA4 fused with IgG1 Fc and Avi-tag (EphA4-Fc) were transfected into 293 Freestyle cells (Invitrogen) for transient expression, and the mouse EphA4-Fc was used for biopanning. Protein purity was judged by SDS-PAGE, and protein concentration was measured spectrophotometrically (NanoVue, GE Healthcare).

Selection, Expression, and Purification of the EphA4-Specific Fabs and Conversion to IgG1s.

A large phage display library constructed using PMBC cDNA from 40 healthy volunteers and another phage display library constructed using cord blood from 10 donors were panned using biotin-labeled mouse EphA4-Fc fusion protein conjugated to magnetic beads (Invitrogen). Amplified libraries of $10^{12}$ phage-displayed Fabs were incubated with 5, 3 and 1 µg of EphA4-Fc for 2 h at room temperature during the first, second and third rounds of biopanning, respectively. Clones that bound to EphA4-Fc were identified from the third round of panning by using polyclonal and monoclonal phage ELISA. The $V_H$ and $V_L$ domains of these clones were sequenced, and dominant clones were identified. For conversion to IgG1, the heavy and light chains of Fabs were amplified and re-cloned into the pDR12 vector (provided by D. Burton, Scripps Research Institute, La Jolla, Calif.). Both Fabs and IgG s were expressed as previously described. Protein purity was estimated as >95% by SDS-PAGE and protein concentration was measured spectrophotometrically (NanoVue, GE Healthcare).

ELISA.

The EphA4 proteins were coated on a 96-well plate (Costar) at 50 ng/well in PBS overnight at 4° C. For phage ELISA, phages from each round of panning (polyclonal phage ELISA) or clones randomly picked from the infected TG 1 cells (monoclonal phage ELISA) were incubated with immobilized antigen. Bound phages were detected with anti-M13-HRP polyclonal Ab (Pharmacia, Piscataway, N.J.). For the soluble Fab binding assay, HRP-conjugated mouse anti-FLAG tag Ab (Sigma-Aldrich) was used to detect Fab binding. For the IgG1 binding assay, HRP-conjugated anti-Fab Ab (Sigma-Aldrich) was used for detection. For competitive ELISA assay, extracellular domain of mouse EphA4 recombinant protein or extracellular domain of mouse EphB2 recombinant protein was pre-coated on the ELISA plate and then incubated with different IgG1s for 1 hr at room temperature. After several washes with DPBS, the EphA4 or EphB2 proteins were then incubated with different biotinylated recombinant mouse ephrin-A/ephrin-B Fc chimera proteins for 1 hr at room temperature. The interaction of EphA4/EphB2 and ephrin-A/ephrin-B was determined via the streptavidin-biotin detection method.

Flow Cytometry.

To measure the interactions of IgG1 with EphA4, aliquots of 293T cells, or 293T cells transfected with mouse EphA4, were incubated with IgG1 or ephrin-A5-Fc in 250 µL of RPMI supplemented with 10% fetal bovine serum for 1 h on ice. Unbound proteins were washed away with medium. The secondary antibody FITC-conjugated anti-human IgG (Fc-specific) antibody (Sigma-Aldrich) was incubated with cells for 30 min. Cells were washed and resuspended in PBS plus 0.5% bovine serum albumin (BSA) for flow cytometry on FACSCALIBUR® (Becton Dickinson).

Immunoprecipitation Assay.

Cultured neurons were lysed in radioimmunoprecipitation assay (RIPA) buffer (1% Triton X-100, 1% sodium deoxycholate, 0.1% SDS, 150 mM NaCl, 10 mM sodium phosphate, 2 mM EDTA, and 0.2% sodium vanadate) with various protease inhibitors. Protein lysates were immunoprecipitated with EphA4 antibody at 4° C. for 2 hrs, followed by incubation with proteinG-Sepharose at 4° C. for 1 hr. The samples were washed with RIPA buffer or buffer A and resuspended in SDS sample buffer. Tyrosine phosphorylation of EphA4 was detected by Western blot analysis using 4G10 antibody.

Immunocytochemical Analysis.

Cultured neurons were fixed by 4% paraformaldehyde and 5% sucrose in PBS. After blocking with 1% bovine serum albumin, 4% goat serum, and 0.1% Triton X-100 (Sigma) for 20 min, the cells were incubated with the corresponding primary antibody overnight at 4° C. and subsequently washed 3 times with 1×PBS. Alexa Fluor secondary antibody was added with 1% bovine serum albumin for 1 h at room temperature in the dark. The cellular localization of EphA4 was analyzed by super resolution imaging system.

EphA4 Clustering.

Rat hippocampal neurons were seeded on 48-well plates coated with poly-D-lysine (50 µg/mL) at 6000 cells per well. Neurons at 3 DIV were pretreated with IgG1 for 20 min and then followed with pre-clustered ephrin-A1 (0.25 µg/ml) for another 40 min. The cells were fixed and immunostained with anti-EphA4 and anti-Tau-1 antibodies to visualize the EphA4 clusters and identity axon. The cellular imaging and quantification of EphA4 clusters were performed using the IN Cell Analyzer 6000 high content assay system (GE Healthcare).

mEPSC.

Cultured hippocampal neurons (~22-26 DIV) were treated with Aβ for 24 h. For mEPSC recordings, cells were held at −70 mV. The pipette resistances for these experiments were typically 3-5 MΩ, while series resistances were 15-20 MΩ. mEPSCs were recorded from each cell for 1 min in each condition. mEPSC's were measured by the Mini Analysis Program for measuring AMPAR EPSCs (Synaptosoft). Only recording epochs in which series and input resistances varied <10% were analyzed.

All patents, patent applications, and other publications, including GenBank Accession Numbers, cited in this application are incorporated by reference in the entirety for all purposes.

What is claimed is:

1. An isolated monoclonal antibody or an antigen binding fragment thereof, comprising:
   a) a heavy chain variable domain comprising the amino acid sequence set forth as SEQ ID NO:3 and a light chain variable domain comprising the amino acid sequence set forth as SEQ ID NO:6; or
   b) a heavy chain variable domain comprising the amino acid sequence set forth as SEQ ID NO:4 and a light chain variable domain comprising the amino acid sequence set forth as SEQ ID NO:7, wherein the monoclonal antibody or antigen binding fragment thereof specifically binds the EphA4 ligand binding domain.

2. The isolated monoclonal antibody of claim 1, wherein the monoclonal antibody is an IgG.

3. The isolated antigen binding fragment of claim 1, wherein the antigen binding fragment is an scFv, Fv, Fab, or F(ab)2 antigen binding fragment.

4. The isolated monoclonal antibody or antigen binding fragment of claim 1, wherein the antibody is conjugated to an effector molecule.

5. The isolated monoclonal antibody or antigen binding fragment of claim 4, wherein the effector molecule is a detectable label, a toxin, or a chemotherapeutic agent.

6. The isolated monoclonal antibody or antigen binding fragment of claim 5, wherein the detectable label is a fluorescent marker, a radiolabel, avidin, biotin, or an enzyme, or wherein the toxin is a *Pseudomonas* exotoxin.

7. The isolated monoclonal antibody or antigen binding fragment thereof of claim 1, wherein the monoclonal antibody is IgG1 m105.

8. A pharmaceutical composition comprising the monoclonal antibody or antigen binding fragment of claim 1 and a pharmaceutically acceptable carrier.

9. A bispecific antibody comprising the monoclonal antibody or antigen binding fragment of claim 1.

10. A polynucleotide sequence encoding the monoclonal antibody or antigen binding fragment of claim 1 optionally operably linked to a promoter.

11. A method of detecting the presence of a tumor in a subject, comprising contacting a biological sample from the subject with an effective amount of the monoclonal antibody or antigen binding fragment of claim 1 and detecting binding of the monoclonal antibody or antigen binding fragment to the biological sample, wherein an increase in binding compared to a control indicates that the subject has the tumor.

12. The method of claim 11, wherein the tumor is a breast carcinoma, esophageal cancer, non-small cell lung cancer, gastric cancer, or pancreatic cancer.

* * * * *